United States Patent [19]
Bao et al.

[11] Patent Number: 6,022,890
[45] Date of Patent: Feb. 8, 2000

[54] IMMUNOSUPPRESSANT TETRACYCLIC TRITERPENES

[75] Inventors: Jianming Bao, Scotch Plains; Robert K. Baker, Cranford; Frank Kayser, Hoboken; Andrew Kotliar, Highland Park; William H. Parsons, Belle Mead; Kathleen M. Rupprecht, Cranford; Peter J. Sinclair, Scotch Plains, all of N.J.

[73] Assignee: Merck & Co., Inc., Rahway, N.J.

[21] Appl. No.: 09/176,541

[22] Filed: Oct. 21, 1998

Related U.S. Application Data

[60] Provisional application No. 60/065,997, Nov. 14, 1997.

[51] Int. Cl.$^7$ .................. A61K 31/335; C07D 303/17
[52] U.S. Cl. ................. 514/475; 514/510; 549/543; 560/127; 560/194
[58] Field of Search .............. 549/543; 514/475, 514/510; 560/127, 194

[56] References Cited

U.S. PATENT DOCUMENTS

| | | | |
|---|---|---|---|
| 3,483,191 | 12/1969 | Krakower et al. | 260/239.57 |
| 3,965,128 | 6/1976 | Furst, et al. | 260/348 C |
| 4,453,967 | 6/1984 | Mori | 71/88 |
| 4,489,206 | 12/1984 | Cava, et al. | 549/543 |
| 5,599,950 | 2/1997 | Teng | 549/297 |
| 5,631,282 | 5/1997 | Goetz | 514/450 |
| 5,679,705 | 10/1997 | Baker et al. | 514/450 |
| 5,696,156 | 12/1997 | Baker et al. | 514/450 |

FOREIGN PATENT DOCUMENTS

| | | |
|---|---|---|
| WO 96/40688 | 12/1996 | WIPO. |
| WO 97/16068 | 5/1997 | WIPO. |
| WO 97/16182 | 5/1997 | WIPO. |
| WO 97/16437 | 5/1997 | WIPO. |
| WO 97/16438 | 5/1997 | WIPO. |
| WO 98/16532 | 4/1998 | WIPO. |

OTHER PUBLICATIONS

Abreu, et al., "A Nor–Triterpenoid From Lophanthera Lactescens", Phytochemistry, vol. 29(7), pp. 2257–2261, 1990.

Sabata et al., "Tetranortriterpenoids and Related Substances. Part 19.1 Revised Structures of Atalantolide and Atalantin, Limonoids from the Root Bark of Atalantia Monophylla Correa (Rutaceae)", J. Chem. Soc. Perkin I, pp. 1876–1877, 1977.

*Primary Examiner*—Evelyn Mei Huang
*Attorney, Agent, or Firm*—J. Antonio Garcia-Rivas; Mark R. Daniel

[57] ABSTRACT

The compounds of Formula I

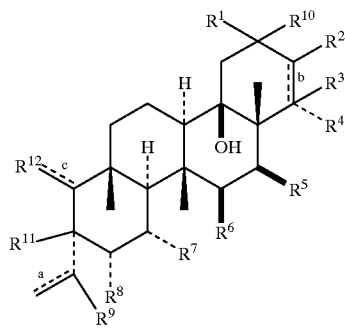

are useful as immunosuppressive agents.

15 Claims, No Drawings

IMMUNOSUPPRESSANT TETRACYCLIC TRITERPENES

This application claims the benefit of provisional application Ser. No. 60/065,997, filed Nov. 14, 1997.

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A (CsA), which was approved by the US Food and Drug Administration in 1983 is currently the leading drug used to prevent rejection of transplanted organs. In 1993, FK-506 (Prograf) was approved by the US FDA for the prevention of rejection in liver transplantation. CsA and FK-506 act by inhibiting the body's immune system from mobilizing its vast arsenal of natural protecting agents to reject the transplant's foreign protein. In 1994, CsA was approved by the US FDA for the treatment of severe psoriasis and has been approved by European regulatory agencies for the treatment of atopic dermatitis. Though they are effective in fighting transplant rejection, CsA and FK-506 are known to cause several undesirable side effects including nephrotoxicity, neurotoxicity, and gastrointestinal discomfort.

Newer, safer drugs exhibiting less side effects are constantly being searched for in the field.

Four active components of *Spachea correa* were recently identified which inhibit thymidine uptake of T cells.

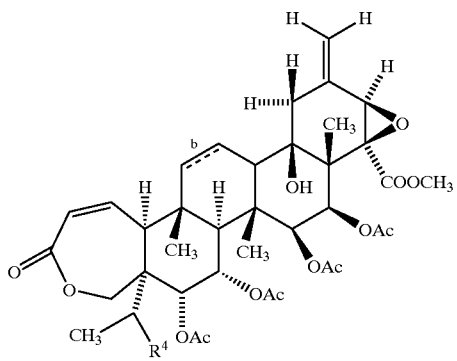

Formula 1(a) b is a single bond and $R^4$ is OAc

Formula 1(b) b is a double bond and $R^4$ is OAc

Formula 1(c) b is a single bond and $R^4$ is OH

Formula 1(d) b is a double bond and $R^4$ is OH

These compounds are useful as immunosuppressive agents in animals, including man. The present invention describes newly developed immunosuppressive compounds derived from the compounds described in Formulae 1(a) through 1(d) and which have the relative stereochemistry depicted above.

SUMMARY OF THE INVENTION

This invention relates to a class of triterpene derivatives of the general structural Formula I

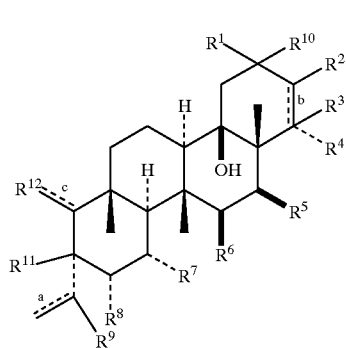

are useful as immunosuppressives.

As an immunosuppressive, the compounds of this invention are useful in the treatment of autoimmune diseases, the prevention of rejection of foreign organ transplants and/or related afflictions, diseases and illnesses. Also within the scope of this invention are pharmaceutical formulations comprising a compound of Formula I and a pharmaceutical carrier, as well as, pharmaceutical formulations comprising a compound of Formula I, and one or more immunosuppressive compounds and a pharmaceutical carrier.

DETAILED DESCRIPTION OF THE INVENTION

A. Scope of the Invention

The present invention is related to compounds of Formula I, including but not limited to those specified in the examples, which are useful in a mammalian subject for the treatment and prevention of the resistance by transplantation of organs or tissue, graft-versus-host diseases brought about by medulla ossium transplantation; rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, bronchial asthma, allergic asthma, intrinsic asthma, extrinsic asthma and dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth; muscular dystrophy; Pyoderma and Sezary's syndrome, Addison's disease, ischemia-reperfusion injury of organs which occurs upon preservation, transplantation or ischemic disease, for example, thrombosis and cardiac infraction, endotoxin-shock, pseudomembranous colitis, colitis caused by drug or radiation, ischemic acute renal insufficiency, chronic renal insufficiency, toxinosis caused by lung-oxygen or drug, for example, paracort and bleomycins, lung cancer, pulmonary emphysema, cataracta, siderosis, retinitis, pigmentosa, senile macular degeneration, vitreal scarring, corneal alkali burn; dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy; disease caused by histamine or leukotriene-C4 release; Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmention of chemotherapeutic effect, preventing or treating activity of cytomegalovirus infection, HCMV infection, and antiinflammatory activity; and treatment of immunodepression or a disorder involving immunodepression, including AIDS, cancer, senile dementia, trauma, chronic bacterial infection, and certain central nervous system disorders.

More particularly, this invention relates to compounds of the general structural Formula I:

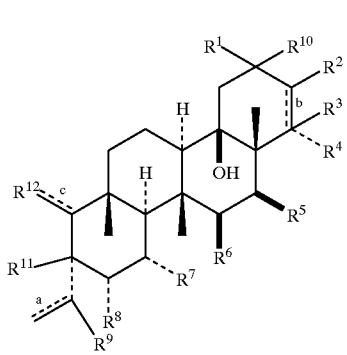

I or a pharmaceutically acceptable salt, crystal form, or hydrate, wherein:

a, b and c are independently a single bond or a double bond, and represented by ==== in the structure above;

n is: 0, 1 or 2;

r is: 0 or 1;

s is: 0 or 1;

$R^1$ and $R^{10}$ are independently:
(1) hydroxyl,
(2) $(C_1-C_6)$-alkyloxy,
(3) H,
(4) $OCO(C_1-C_6)$-alkyl,
(5) $(C_1-C_6)$-alkyl,
(6) $R^1$ and $R^{10}$ taken together is an exo-methylene group,
(7) $R^1$ and $R^{10}$ taken together is =O, or
(8) $R^1$ and $R^{10}$ taken together is an oxirane group;

$R^2$ and $R^3$ are independently:
(1) hydroxyl,
(2) $(C_1-C_6)$-alkyloxy,
(3) H,
(4) $OCO(C_1-C_6)$-alkyl,
(5) $(C_1-C_6)$-alkyl,
(6) phenyl, or
(7) $R^2$ and $R^3$ taken together is an oxirane group when b is a single bond, additionally, $R^2$ can be =O when b is a single bond;

R4 is:
(1) $CO_2(C_1-C_6)$-alkyl,
(2) $CO_2H$,
(3) $CH_2OH$,
(4) $C(=O) NR^{13}R^{14}$, (5) $(C_1-C_6)$-alkyl,
(6) $CH_2O$ $(C_1-C_6)$-alkyl, or
(7) CHO;

$R^5$, $R^6$, $R^7$ and $R^8$ are independently selected from the group consisting of:
(1) $O[(C=O)O_r]_s R^{13}$,
(2) $O[(C=O)O_r]_s$-aryl, aryl as defined below, and
(3) $O[(C=O)O_r]_s$-heteroaryl, heteroaryl as defined below;

$R^9$ is:
(1) H,
(2) OH,
(3) =O when a is a single bond,
(4) $O[(C=O)O_r]_s(C_1-C_6)$-alkyl, alkyl as defined below,
(5) $O[(C=O)O_r]_s(C_2-C_6)$-alkenyl, as defined below,
(6) $O[(C=O)O_r]_s$-aryl, aryl as defined below,
(7) $O[(C=O)O_r]_s$-heteroaryl, heteroaryl as defined below,
(8) $O(CH_2)_n$-heteroaryl, heteroaryl as defined below, or
(9) $O(CH_2)_n$-aryl, aryl as defined below, $R^{11}$ is chosen from the group consisting of:
(1) H,
(2) $O(CH_2)_n$-heteroaryl, wherein heteroaryl is defined as an unsubstituted, monosubstituted, or disubstituted five or six membered aromatic heterocycle containing from 1 to 3 heteroatoms selected from the group consisting of O, N and
S and wherein the substituents are selected from the group consisting of:
  (a) halo, wherein halo is fluoro, chloro, bromo, or iodo,
  (b) hydroxy,
  (c) $(C_1-C_6)$-alkyl,
  (d) $(C_1-C_4)$-perfluoroalkyl,
  (e) $(C_1-C_6)$-alkenyl,
  (f) $(C_1-C_6)$-alkynyl,
  (g) $(C_1-C_6)$-alkyloxy,
  (h) $(C_1-C_6)$-alkyl-$S(O)_n$-,
  (i) phenyl,
  (j) phenoxy,
  (k) cyano,
  (l) nitro,
  (m) $CO_2H$,
  (n) $CO(C_1-C_6)$-alkyl,
  (o) $CO_2(C_1-C_6)$-alkyl,
  (p) $CONR^{13}R^{14}$,
  (q) $NR^{13}R^{14}$,
  (r) $NR^{13}CO(C_1-C_6)$-alkyl,
  (s) fused benzo, and
  (t) fused pyridyl group,
(3) $O(CH_2)_n$-aryl, wherein aryl is defined as phenyl or naphthyl, unsubstituted or substituted with one, two or three of the substituents selected from the group consisting of:
  (a) halo, wherein halo is fluoro, chloro, bromo, or iodo,
  (b) hydroxy,
  (c) $(C_1-C_6)$-alkyl,
  (d) $(C_1-C_4)$-perfluoroalkyl,
  (e) $(C_1-C_6)$-alkenyl,
  (f) $(C_1-C_6)$-alkynyl,
  (g) $(C_1-C_6)$-alkyloxy,
  (h) $(C_1-C_6)$-alkyl-$S(O)_n$-,
  (i) phenyl,
  (j) phenoxy,
  (k) cyano,
  (l) nitro,
  (m) $CO_2H$,
  (n) $CO(C_1-C_6)$-alkyl,
  (o) $CO_2(C_1-C_6)$-alkyl,
  (p) $CONR^{13}R^{14}$,
  (q) $NR^{13}R^{14}$,
  (r) $NR^{13}CO(C_1-C_6)$-alkyl,
  (s) $(C_1-C_6)$-alkenyloxy, and
  (t) benzyloxy;
(4) $(C_1-C_6)$-alkyl, wherein alkyl is unsubstituted or substituted with one or two of the substituents selected from the group consisting of:
  (a) halo, wherein halo is fluoro, chloro, bromo, or iodo,
  (b) hydroxy,
  (c) oxo,
  (d) $(C_1-C_6)$-alkyloxy,
  (e) $(C_1-C_6)$-$S(O)_n$-,
  (f) aryl-$(C_1-C_6)$-alkyloxy,
  (g) cyano,
  (h) nitro,
  (i) vinyl,
  (j) $NR^{13}R^{14}$,
  (k) $NR^{13}CO(C_1-C_6)$-alkyl,
  (l) CHO,
  (m) $CO_2H$,
  (n) $CO(C_1-C_6)$-alkyl,
  (o) $CO_2(C_1-C_6)$-alkyl,
  (p) $CONR^{13}R^{14}$,
  (q) aryl, as defined above, and
  (r) $OCOCH_3$,
(5) $(CH_2)_n O(C_1-C_6)$-alkyl, wherein alkyl is as defined above,
(6) $(C_2-C_6)$-alkenyl, wherein alkenyl is unsubstituted or substituted with one or two of the substituents selected from the group consisting of:
  (a) halo, wherein halo is fluoro, chloro, bromo, or iodo,
  (b) hydroxy,
  (c) oxo,
  (d) $(C_1-C_6)$-alkyloxy,
  (e) $(C_1-C_6)$-$S(O)_n$-,
  (f) phenyl-$(C_1-C_6)$-alkyloxy,
  (g) cyano,
  (h) nitro,
  (i) vinyl,
  (j) $NR^{13}R^{14}$,
  (k) $NR^{13}CO(C_1-C_6)$-alkyl,
  (l) CHO,
  (m) $CO_2H$,
  (n) $CO(C_1-C_6)$-alkyl,
  (o) $CO_2(C_1-C_6)$-alkyl,
  (p) $CONR^{13}R^{14}$,
  (q) aryl, wherein aryl is as defined above,
  (r) heteroaryl, wherein heteroaryl is as defined above, and
  (s) $OCOCHC_3$,
(7) $(CH_2)_n O(C_2-C_6)$-alkenyl, wherein alkenyl is as defined above,
(8) CHO,
(9) COOH,
(10) $CONR^{13}R^{14}$,
(11) $O[(C=O)O_r]_s(C_1-C_6)$-alkyl, alkyl as defined above,
(12) $(CH_2)_n S(C_1-C_6)$-alkyl, wherein alkyl is as defined above,

(13) $(CH_2)_nS(C_2-C_6)$-alkenyl, wherein alkenyl is as defined above, or
(14) $(CH_2)_nS(C_2-C_6)$-aryl, wherein aryl is as defined above;

$R^{12}$ is as defined above for $R^{11}$ when c is a single bond, or $R^{12}$ is as defined below when c is a double bond:
(1) =O,
(2) =CH—$(C_1-C_6)$-alkyl, wherein alkyl is as defined above,
(3) =CH—$(C_1-C_8)$-alkenyl, wherein alkenyl is as defined above, or
(4) =CH-aryl, wherein aryl is as defined above;

$R^{13}$ and $R^{14}$ are independently:
(1) hydrogen,
(2) $(C_1-C_6)$-alkyl, or
(3) phenyl.

A subembodiment of the invention is the compound of structural Formula I as defined above, wherein b is a single bond;

$R^1$ and $R^{10}$ are independently:
(1) hydroxyl,
(2) $(C_1-C_6)$-alkyl,
(3) $R^1$ and $R^{10}$ taken together is an exo-methylene group,
(4) $R^1$ and $R^{10}$ taken together is =O, or
(5) $R^1$ and $R^{10}$ taken together is an oxirane group;

$R^2$ and $R^3$ are taken together to be an oxirane group;

R4 is:
(1) $CO_2(C_1-C_6)$-alkyl, wherein alkyl is defined above, or
(2) $CH_2O(C_1-C_6)$-alkyl;

$R^5$, $R^6$, $R^7$ and $R^8$ are $OCO(C_1-C_6)$-alkyl;

$R^9$ is:
(1) $O[(C=O)O_r]_s(C_1-C_6)$-alkyl, alkyl as defined below,
(2) $O[(C=O)O_r]_s(C_2-C_6)$-alkenyl, as defined below,
(3) $O[(C=O)O_r]_s$-aryl, aryl as defined below,
(4) $O[(C=O)O_r]_s$-heteroaryl, heteroaryl as defined below,
(5) $O(CH_2)_n$-heteroaryl, heteroaryl as defined below, or
(6) $O(CH_2)_n$-aryl, aryl as defined below, $R^{11}$ and $R^{12}$ are independently chosen from the group consisting of:
(1) H,
(2) $O(CH_2)$n-aryl, wherein aryl is defined as phenyl or naphthyl, unsubstituted or substituted with one, two or three of the substituents selected from the group consisting of:
  (a) halo, wherein halo is fluoro, chloro, bromo, or iodo,
  (b) hydroxy,
  (c) $(C_1-C_6)$-alkyl,
  (d) $(C_1-C_4)$-perfluoroalkyl,
  (e) $(C_1-C_6)$-alkyloxy,
  (f) cyano, and
  (g) nitro,
(3) $(C_1-C_6)$-alkyl, wherein alkyl is unsubstituted or substituted with one or two of the substituents selected from the group consisting of:
  (a) halo, wherein halo is fluoro, chloro, bromo, or iodo,
  (b) hydroxy,
  (c) oxo,
  (d) $(C_1-C_6)$-alkyloxy,
  (e) CHO,
  (f) $CO_2H$,
  (g) $CO_2(C_1-C_6)$-alkyl,
  (h) $CONR^{13}R^{14}$,
  (i) aryl, as defined above, and
  (j) $OCOCH_3$,
(4) $(CH_2)_nO(C_1-C_6)$-alkyl, wherein alkyl is as defined above,
(5) $(C_2-C_6)$-alkenyl, wherein alkenyl is unsubstituted or substituted with one or two of the substituents selected from the group consisting of:
  (a) halo, wherein halo is fluoro, chloro, bromo, or iodo,
  (b) hydroxy,
  (c) oxo,
  (d) $(C_1-C_6)$-alkyloxy,
  (e) CHO,
  (f) $CO_2H$,
  (g) $CO_2(C_1-C_6)$-alkyl,
  (h) $CONR^{13}R^{14}$,
  (i) aryl, as defined above, and
  (j) $OCOCH_3$,
(6) $(CH_2)_nO(C_2-C_6)$-alkenyl, wherein alkenyl is as defined above,
(7) CHO,
(8) COOH,
(9) $CONR^{13}R^{14}$,
(10) $O[(C=O)O_r]_s(C_1-C_6)$-alkyl, alkyl as defined above,
(11) $(CH_2)_nS(C_1-C_6)$-alkyl, wherein alkyl is as defined above,
(12) $(CH_2)_nS(C_2-C_6)$-alkenyl, wherein alkenyl is as defined above, or
(13) $(CH_2)_nS(C_2-C_6)$-aryl, wherein aryl is as defined above;

$R^{12}$ can also be any of the following when c is a double bond:
(1) =O,
(2) =CH—$(C_1-C_6)$-alkyl, wherein alkyl is as defined above,
(3) =CH—$(C_1-C_6)$-alkenyl, wherein alkenyl is as defined above, or
(4) =CH—$(C_1-C_6)$-aryl, wherein aryl is as defined above;

$R^{13}$ and $R^{14}$ are independently:
(1) hydrogen,
(2) $(C_1-C_6)$-alkyl, or
(3) phenyl.

A preferred embodiment of the invention is the compound of structural Formula I as defined above, wherein $R^1$ and $R^{10}$ are independently:
(1) $(C_1-C_3)$-alkyl,
(2) $R^1$ and $R^{10}$ taken together is an exo-methylene group,
(3) $R^1$ and $R^{10}$ taken together is =O, or
(4) $R^1$ and $R^{10}$ taken together is an oxirane group;

$R^2$ and $R^3$ are taken together to be an oxirane group;

R4 is:
(1) $CO_2(C_1-C_3)$-alkyl, wherein alkyl is methyl, ethyl, or propyl, or
(2) $CH_2O(C_1-C_3)$-alkyl, wherein alkyl is methyl, ethyl, or propyl;

$R^5$, $R^6$, $R^7$ and $R^8$ are $O(C=O)CH_3$;

$R^9$ is:
(1) $O(C=O)(C_1-C_3)$-alkyl, wherein alkyl is methyl, ethyl, or propyl, or (6) O(CH$_2$)-aryl, wherein aryl is phenyl or naphthyl unsubstituted or substituted with one or two substitutents selected from the following: F, Cl, Br, I, methyl, ethyl, propyl, and hydroxyl;

$R^{11}$ and $R^{12}$ are independently chosen from the group consisting of:
(1) O(CH$_2$)-phenyl, wherein phenyl is unsubstituted or substituted with one or two of the substituents selected from the group consisting of:
  (a) halo, wherein halo is fluoro, chloro, bromo, or iodo,
  (b) hydroxy,
  (c) (C$_1$–C$_6$)-alkyl,
  (d) (C$_1$–C$_4$)-perfluoroalkyl,
  (e) (C$_1$–C$_6$)-alkyloxy,
  (f) cyano, and
  (g) nitro,
(2) (C$_1$–C$_3$)-alkyl, wherein alkyl is unsubstituted or substituted with one or two of the substituents selected from the group consisting of:
  (a) halo, wherein halo is fluoro, chloro, bromo, or iodo,
  (b) hydroxy,
  (c) oxo,
  (d) (C$_1$–C$_3$)-alkyloxy,
  (e) CHO,
  (f) CO$_2$H,
  (g) CO$_2$(C$_1$–C$_3$)-alkyl, wherein alkyl is methyl, ethyl, or propyl,
  (h) CONR$^{13}$R$^{14}$,
  (i) phenyl, as defined above, and
  (j) OCOCH$_3$,
(3) (CH$_2$)O(C$_1$–C$_3$)-alkyl, wherein alkyl is methyl, ethyl, or propyl,
(4) (C$_2$–C$_3$)-alkenyl, wherein alkenyl is unsubstituted or substituted with one or two of the substituents selected from the group consisting of:
  (a) halo, wherein halo is fluoro, chloro, bromo, or iodo,
  (b) hydroxy,
  (c) oxo,
  (d) (C$_1$–C$_6$)-alkyloxy,
  (e) CHO,
  (f) CO$_2$H,
  (g) CO$_2$(C$_1$–C$_6$)-alkyl,
  (h) CONR$^{13}$R$^{14}$,
  (i) aryl, as defined above, and
  (j) OCOCH$_3$,
(5) (CH$_2$)O(C$_2$–C$_3$)-alkenyl, wherein alkenyl is defined as vinyl or allyl,
(6) CHO,
(7) COOH,
(8) CONR$^{13}$R$^{14}$, and
(9) O(C=O)H;

$R^{12}$ can also be any of the following when c is a double bond:
(1) =O, or
(2) =CH—(C$_1$–C$_3$)-alkyl, wherein alkyl is as defined above, $R^{13}$ and $R^{14}$ are independently:
(1) hydrogen,
(2) (C$_1$–C$_3$)-alkyl, wherein alkyl is defined as methyl, ethyl, or propyl, or
(3) phenyl.

Another preferred embodiment of the invention is a compound selected from the group consisting of:

[1a-R-1aα, 2β, 3aβ, 3β, 5aβ, 6β, 7α, 7β, 8α, 9α, 9aα, 9aα, 9bβ, 10β, 11β, 11aβ, 11bα, 11b β]-7-(1-R-acetoxyethyl)-3a-hydroxy-6, 7-bis-(hydroxymethyl)-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β5aβ, 6β, 7α, 7β, 8α, 9α9aα, 9bβ, 10β, 11β, 11aβ, 11bα, 11bβ] -7-(1-R-acetoxyethyl)-2-epoxymethylidene-3a-hydroxy-6, 7-bis-(hydroxymethyl)-11b-methoxycarbonyl-8, 9, 10, 11-tetraacetoxy-5a, 9b, 11a-trimethyl-1a, 3, 3a, 3b, 4, 5, 5a, 6, 7, 8, 9, 9a, 9b, 10, 11, 11a, 11b-hexadecahydrocryseno [1,2-b] oxirene,

[1a-R-1aα, 2β, 3aβ, 3β5aβ, 6β, 7α, 7β, 8α, 9α9aα, 9bβ, 10β, 11β, 11aβ, 11bα, 11bβ]-7-(1-R-acetoxyethyl)-3a-hydroxy-6-formyl-7-((2-acetoxyacetoxy) methyl)-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno [1,2-b] oxirene,

[1a-R-1aα, 2β, 3aβ, 3β5aβ, 6β, 7α, 7β, 8α, 9α9aα, 9bβ, 10β, 11β, 11aβ, 11bα, 11bβ]-7-(1-R-acetoxyethyl)-3a-hydroxy-6-formyl-7-(2-hydroxy-acetoxymethyl)-11b-methoxycarbonyl-2-oxo-8, 9, 10, 11-tetraacetoxy-5a, 9b, 11a-trimethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β5aβ, 6β, 7α, 7β, 8α, 9α9aα, 9bβ, 10β, 11β, 11aβ, 11bα, 11bβ]-7-(1-R-acetoxyethyl)-3a-hydroxy-6, 7-bis-(acetoxymethyl)-11b-methoxycarbonyl-2, 8, 9, 10, 11-pentaacetoxy-5a, 9b, 11a-trimethyl-1a, 2, 3, 3a, 3b, 4, 5, 5a, 6, 7, 8, 9, 9a, 9b, 10, 11, 11a, 11b-octadecahydrocryseno [1,2-b]oxirene,

[1a-R-1aα, 2β, 3aβ, 3β5aβ, 6β, 7α, 7β, 8α, 9α9aα, 9bβ, 10β, 11β, 11aβ, 11bα, 11bβ]-7-(1-R-acetoxyethyl)-3a-hydroxy-7-(2-acetoxyydroxymethyl)-6-(3-methoxy-3-oxopropylidene)-11b-methoxycarbonyl-2-oxo-8, 9, 10, 11 -tetraacetoxy-5a, 9b, 11a-trimethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β5aβ, 6β, 7α, 7β, 8α, 9α9aα, 9bβ, 10β, 11β, 11aβ, 11bα, 11bβ]-7-(1-R-acetoxyethyl)-3a-hydroxy-6, 7-bis-(methoxymethyl)-11b-ethoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β5aβ, 6β, 7α, 7β, 8α, 9α9aα, 9bβ, 10β, 11β, 11aβ, 11bα, 11bβ]-7-(1-R-acetoxyethyl)-3a-hydroxy-6-methoxymethyl-7-hydroxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β5aβ, 6β, 7α, 7β, 8α, 9α9aα, 9bβ, 10β, 11β, 11aβ, 11bα, 11bβ]-7-(1-R-acetoxyethyl)-3a-hydroxy-6-hydroxymethyl-7-methoxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β5aβ, 6β, 7α, 7β, 8α, 9α9aα, 9bβ, 10β, 11β, 11aβ, 11bα, 11bβ]-7-(1-R-acetoxyethyl)-3a-hydroxy-6-methoxymethyl-7-ethoxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno [1,2-b]oxirene,

[1a-R-1aα, 2β, 3aβ, 3β5aβ, 6β, 7α, 7β, 8α, 9α9aα, 9bβ, 10β, 11β, 11aβ, 11bα, 11bβ] -7-(1-R-acetoxyethyl)-3a-hydroxy-6-methoxymethyl-7-benzyloxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β5aβ, 6β, 7α, 7β, 8α, 9α9aα, 9bβ, 10β, 11β, 11aβ, 11bα, 11bβ]-7-(1-R-acetoxyethyl)-3a- hydroxy-6-methoxymethyl-7-allyloxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno [1,2-b]oxirene,

[1a-R-1aα, 2β, 3aβ, 3β5aβ, 6β, 7α, 7β, 8α, 9α9aα, 9bβ, 10β, 11β, 11aβ, 11bα, 11bβ]-7-(1-R-acetoxyethyl)-3a-hydroxy-6-methoxymethyl-7-acetoxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β5aβ, 6β, 7α, 7β, 8α, 9α9aα, 9bβ, 10β, 11β, 11aβ, 11bα, 11bβ]-7-( 1-R-acetoxyethyl)-3a-hydroxy-6-ethoxymethyl-7-methoxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β5aβ, 6β, 7α, 7β, 8α, 9α9aα, 9bβ, 10β, 11β, 11aβ, 11bα, 11bβ]-7-(1-R-(2-bromobenzyloxyethyl)-3a-hydroxy-6, 7-bis-(methoxymethyl)-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β5aβ, 6β, 7α, 7β, 8α, 9α9aα, 9bβ, 10β, 11β, 11aβ, 11bα, 11bβ]-7-(1-R-acetoxyethyl)-3a-hydroxy-6, 7, 11b-tris-(methoxymethyl)-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene, and

[1a-R-1aα, 2β, 3aβ, 3β5aβ, 6β, 7α, 7β, 8α, 9α9aα, 9bβ, 10β, 11β, 11aβ, 11bα, 11bβ]-7-(1-R-acetoxyethyl)-3a-hydroxy-6-oxo-7-methoxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno [1,2-b]oxirene.

A most preferred embodiment of the invenntion is the compound of structural Formula II.

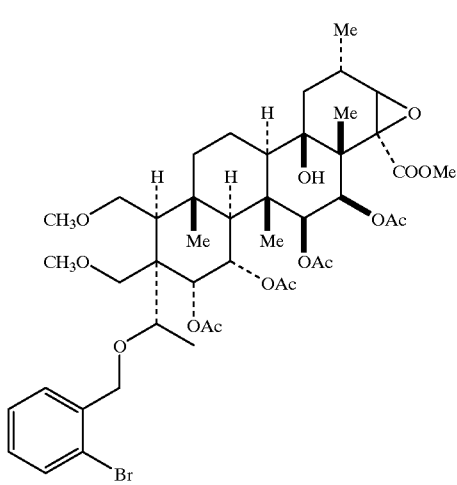

Another most preferred embodiment of the invention is the compound of structural Formula III.

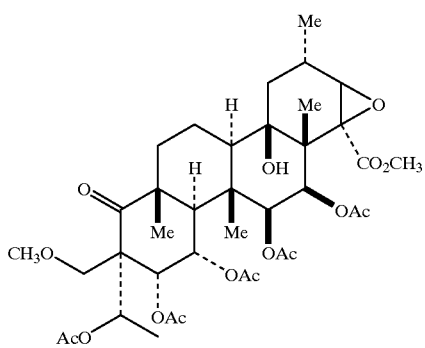

The compounds of the present invention have asymmetric centers and this invention includes all of the optical isomers and mixtures thereof.

In addition compounds with carbon-carbon double bonds may occur in Z- and E- forms with all isomeric forms of the compounds being included in the present invention.

As used herein, the term "alkyl", unless otherwise indicated, includes those alkyl groups of a designated number of carbon atoms of either a straight, branched, or cyclic configuration. Examples of "alkyl" include methyl, ethyl, propyl, isopropyl, butyl, sec-and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy.

"Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethyl pentenyl, and the like, and includes E and Z forms, where applicable. "Halogen", as used herein, means fluoro, chloro, bromo and iodo.

The term "aryl" is defined as a phenyl or naphthyl ring which is optionally substituted with the substituents listed above at any available carbon atoms. The aryl may also be substituted with a fused 5-, 6-, or 7-membered ring containing one or two oxygens and the remaining ring atoms being carbon, the fused 5-, 6-, or 7-ring being selected from the group consisting of: dioxolanyl, dihydrofuranyl, dihydropyranyl, and dioxanyl.

The term "heteroaryl" as utilized herein, unless specifically defined otherwise, is intended to include the following: a 5 or 6-membered ring substituted with one, two or three heteroatoms selected from O, S, N, and is unsubstituted or substituted with one, two or three substituents selected from the group consisting of: Br, Cl, F, I, $(C_1-C_6)$-alkoxy, cyano, nitro, hydroxy, CHO, $CO_2H$, $COC_1-C_6$-alkyl, $CO_2C_1-C_6$-alkyl, $CONR^{13}R^{14}$, $NR^{13}R^{14}$, $NR^{13}COC_1-C_6$-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, pyrazinyl, pyridazinyl, pyridinyl, pyrimidinyl, and pyrrolyl which are substituted or unsubstituted as defined above.

In the compounds of Formula I, the heteroaryl group may be optionally substituted with the substituents listed above at any available carbon atom or nitrogen atom (if present), but compounds bearing certain substitutents, directly substituted to a nitrogen may be relatively unstable and are not preferred. The heteroaryl may also be fused to a second 5-, 6-, or 7-membered ring containing one or two oxygens such as: dioxolanyl, dihydrofuranyl, dihydropyranyl, and dioxanyl.

Pharmaceutically acceptable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydroscopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

As seen in Scheme A, the exocyclic olefin of compound Ia [(4,6,7,15,16-pentakis(acetyloxy)-21,22-epoxy-18-hydroxy-22-methyoxycarbonyl [6α,7α,15β,16β,21β,22β] D:A-Freido-A-homo-27,30-dinor-24-oxaoleana-1, 20(29)-dien-3-one] can be selectively cleaved in two steps. The olefin is first ozonized under standard conditions. Reduction of the intermediate ozonide with an agent such as methyl sulfide gives the ketone intermediate.

REACTION SCHEME A

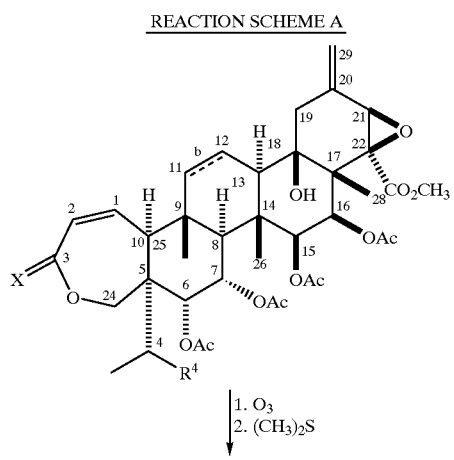

As seen in Scheme B, the exocyclic olefin of compound Ia [(4,6,7,15,16-pentakis(acetyloxy)-21,22-epoxy-18-hydroxy-22-methyoxycarbonyl[6α, 7α, 15β,16β,21β,22β] D:A-Freido-A-homo-27,30-dinor-24-oxaoleana-1, 20(29)-dien-3-one] can be selectively cleaved in two steps. The lactone and the olefin are first ozonized under standard conditions. Reduction of the intermediate ozonides with an agent such as hydrogen and palladium gives the ketone intermediate.

REACTION SCHEME B

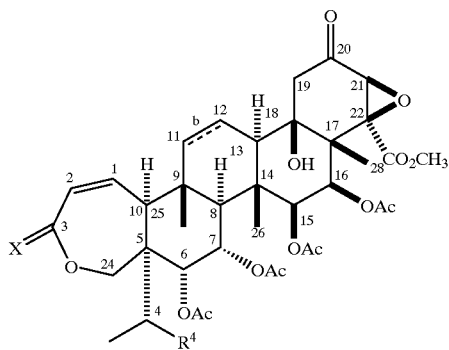

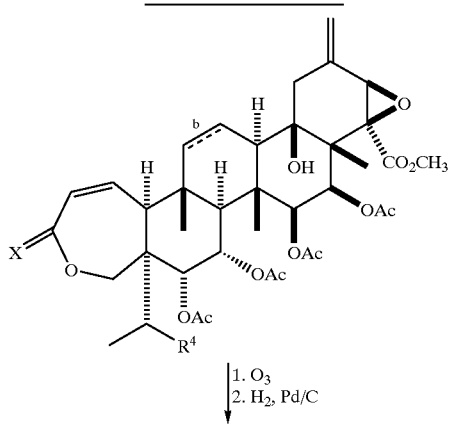

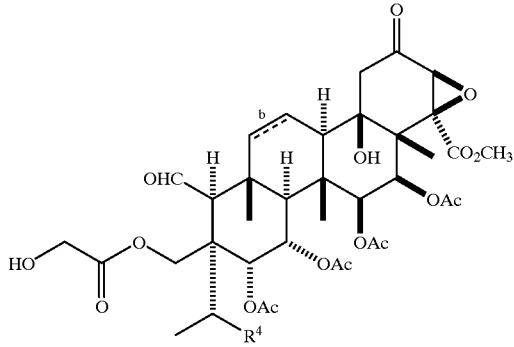

As seen in Reaction Scheme C, compound Ia [(4,6,7,15, 16-pentakis(acetyloxy)-21,22-epoxy-18-hydroxy-22-methyoxycarbonyl [6α,7α,15β,16β,21β, 22β]D :A-Freido-A-homo-27,30-dinor-24-oxaoleana-1,20(29)-dien-3-one]

can be selectively hydrogenated at the C20(29) olefin to give the methyl analog. This conversion can be achieved by hydrogenation with tris(triphenylphosphine)rhodium(I) chloride (Wilkinson's catalyst) in THF at about 50 psi for approximately 24 hours.

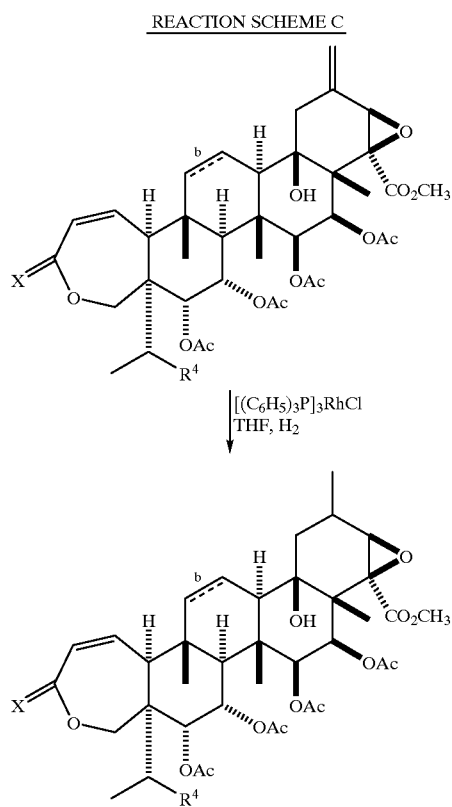

As seen in Scheme D, the exocyclic olefin of compound Ia [(4,6,7,15,16-pentakis(acetyloxy)-21,22-epoxy-18-hydroxy-22-methyoxycarbonyl [6α, 7α, 15β, 16β, 21β, 22β]D:A-Freido-A-homo-27,30-dinor-24-oxaoleana-1,20(29)-dien-3-one] can be selectively cleaved in two steps. The lactone and the olefin are first ozonized under standard conditions. Reduction of the intermediate ozonides with an agent such as hydrogen and palladium gives the ketone intermediate.

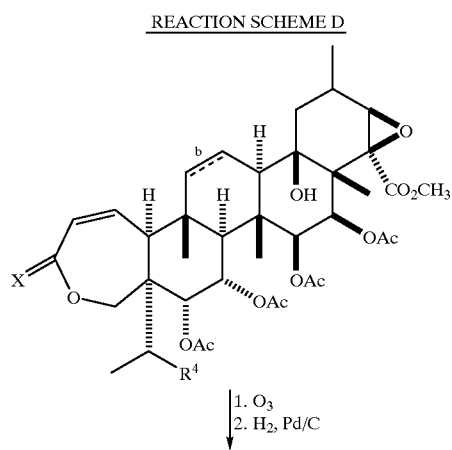

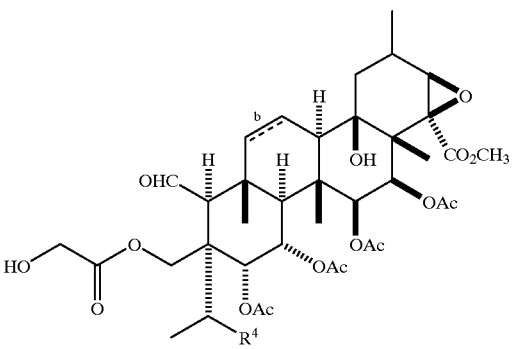

As seen in Scheme E, the exocyclic olefin can be selectively oxidized to the epoxide with a reagent such as m-chloroperbenzoic acid.

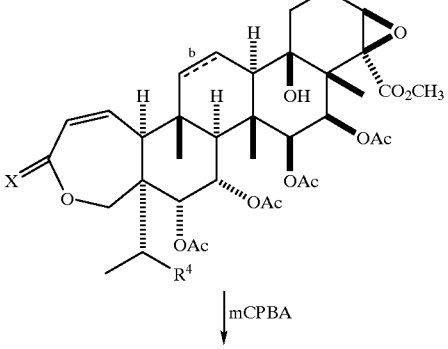

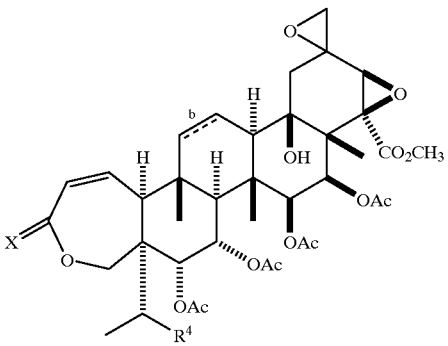

As seen in Scheme F, the lactone group can be cleaved in two steps. The lactone is first ozonized under standard conditions. Reduction of the intermediate ozonide with an agent such as sodium borohydride gives the diol intermediate.

REACTION SCHEME F

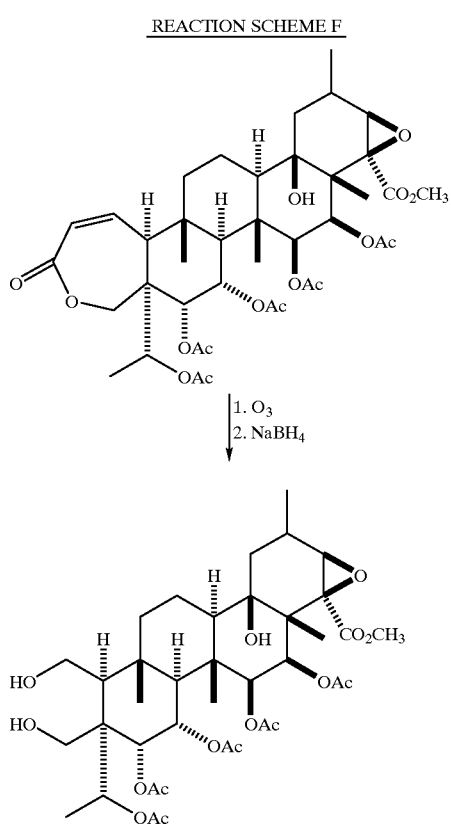

As seen in Scheme G, the lactone group can be opened by catalytic hydrogenation in an alcoholic solvent

REACTION SCHEME G

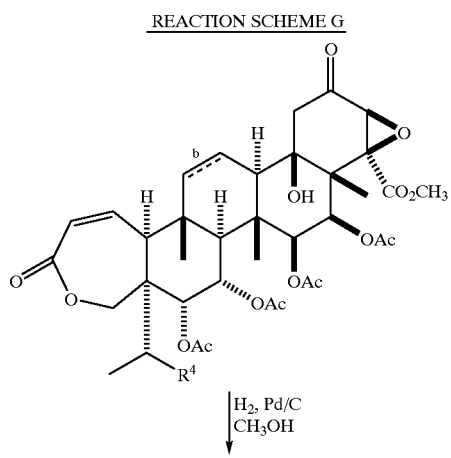

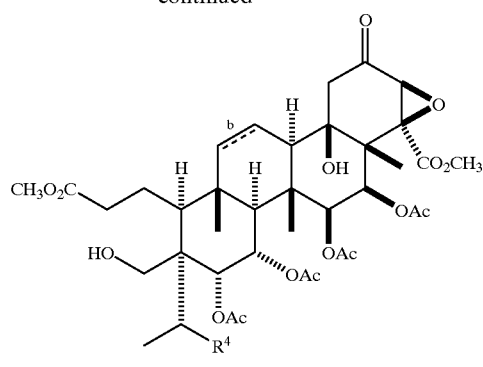

As seen in Scheme H, the lactone group can be opened by treatment with a reagent such as lithium hydroperoxide in tetrahydrofuran followed by esterification with diazomethane.

REACTION SCHEME H

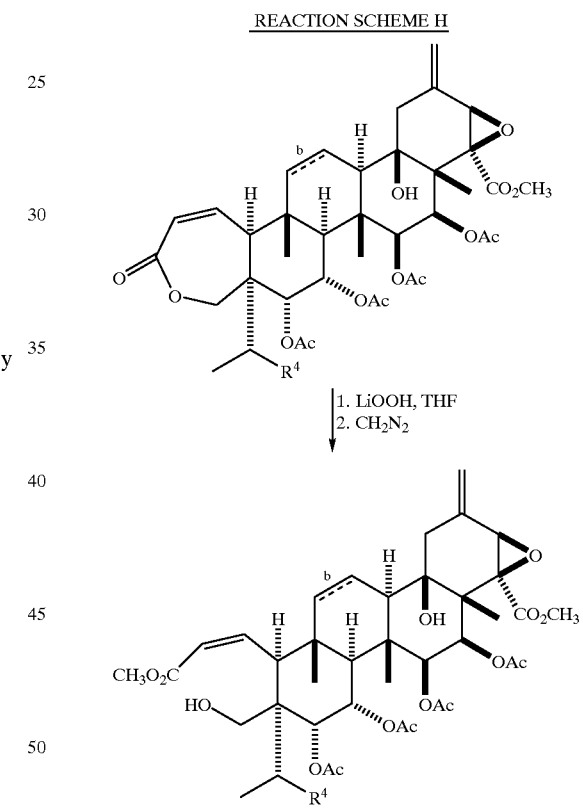

As shown in Scheme I, the hydroxy groups may be acylated by treatment with reagents such as acetic anhydride and pyridine.

REACTION SCHEME I

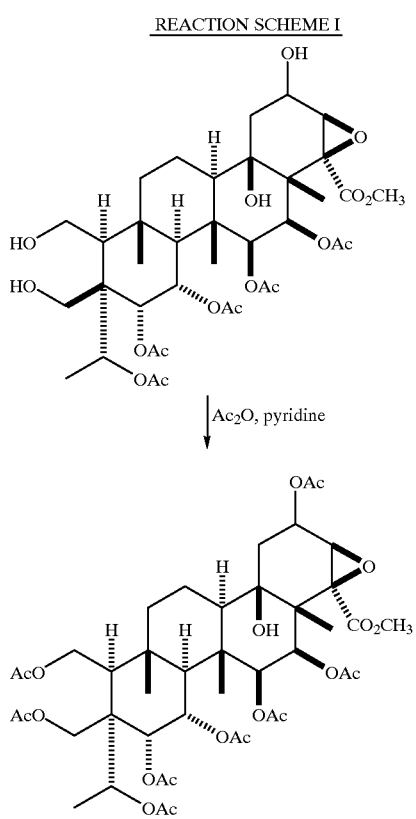

Ac₂O, pyridine

The hydroxy groups may be monoalkylated at either position or dialkylated by reagents such as alkyl trifluoromethanesulfonates and 2,6-di-t-butyl pyridine. Alternatively, as shown in Scheme J, the hydroxy groups may be alkylated sequentially to afford different substitutions. This can be accomplished by using two different alkyl trifluoromethanesulfonates and 2,6-di-t-butyl pyridine as shown.

REACTION SCHEME J

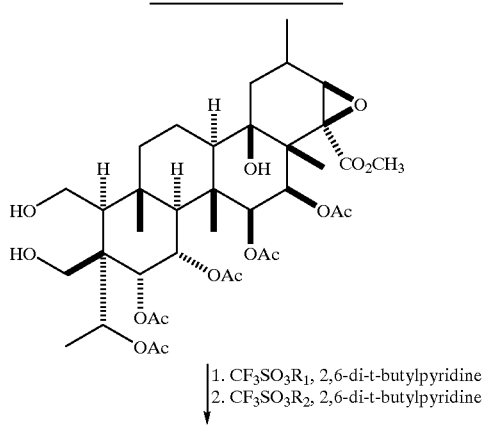

1. $CF_3SO_3R_1$, 2,6-di-t-butylpyridine
2. $CF_3SO_3R_2$, 2,6-di-t-butylpyridine

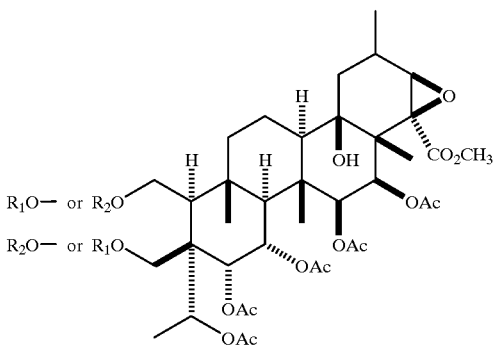

As shown in Reaction Scheme K, compound Ia can be partially reduced to the lactol with reagents such as LiHAl (OtBu)3, Red-Al, or DIBAL-H. The intermediate hydroxy compound can be eliminated to the A-ring-diene by treatment with standard dehydrating reagents. A complex of $FeCl_3$ on silica gel is particularly effective for this transformation. Oxidation of the diene with ozone and catalytic hydrogenation of the ozonide with Pd/C affords the $C_1$–$C_{10}$ olefins where R1=—$CO_2CH_3$ and —OH and R2=—OH and —OCHO. All new hydroxy groups can be acylated as described in Reaction Scheme I.

REACTION SCHEME K

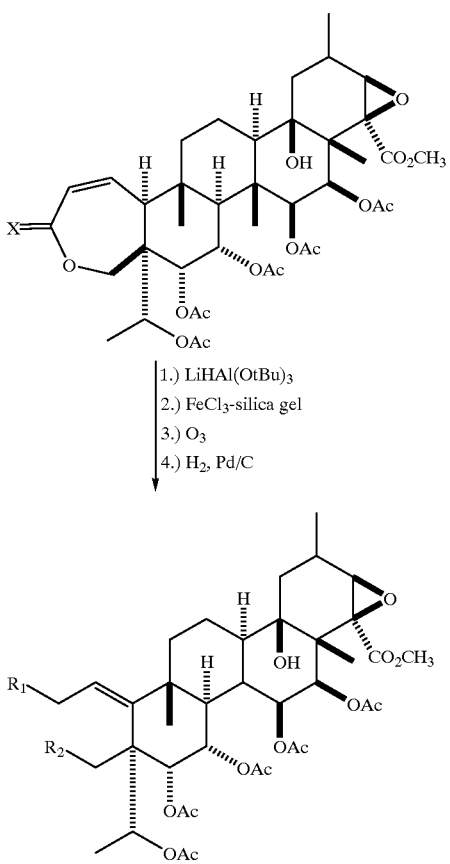

1.) LiHAl(OtBu)₃
2.) FeCl₃-silica gel
3.) O₃
4.) H₂, Pd/C

As shown in Scheme L, open A-ring derivatives variously modified at $R^1$, $R^5a$ and C20, can be selectively de-acetylated at C4 to give the corresponding alcohol by reaction with an aqueous solution of HCl (preferably 2M to 3M concentration) in THF at 45° C. De-acetylation can also be achieved by reacting with $CH_3(Cl)Al[N(OCH_3)CH_3$ (Weinreb reagent) in inert solvents such as THF, toluene or methylene chloride.

REACTION SCHEME L

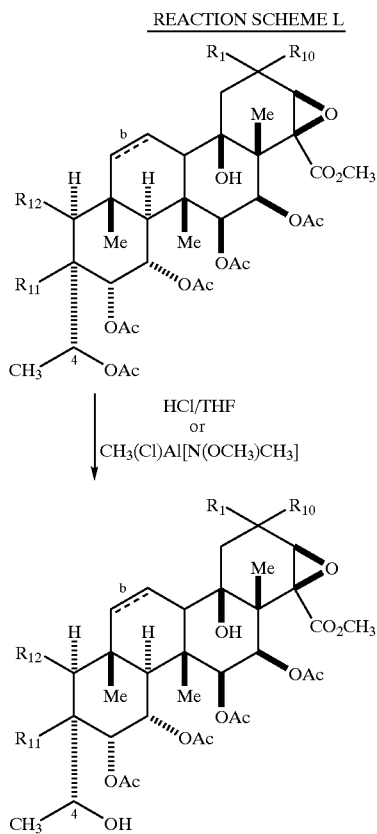

The C4 hydroxy group can be oxidized to the corresponding ketone by a variety of oxidizing agents. The Jones reagent (chromic acid and sulfuric acid in $H_2O$), pyridinium chlorochromate, and oxalyl chloride plus DMSO all will achieve this conversion.

REACTION SCHEME M

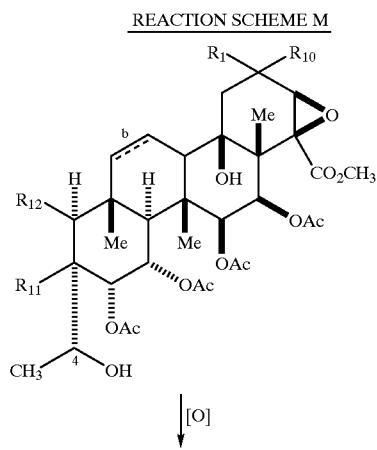

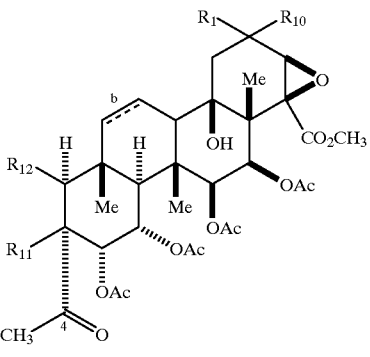

The C4 hydroxy group can also be dehydrated to give the olefin (Scheme N). Reaction of the alcohol with tris-phenoxymethylphosphonium iodide in hexamethylphosphorous triamide (HMPT) at 75° C. will achieve this conversion.

REACTION SCHEME N

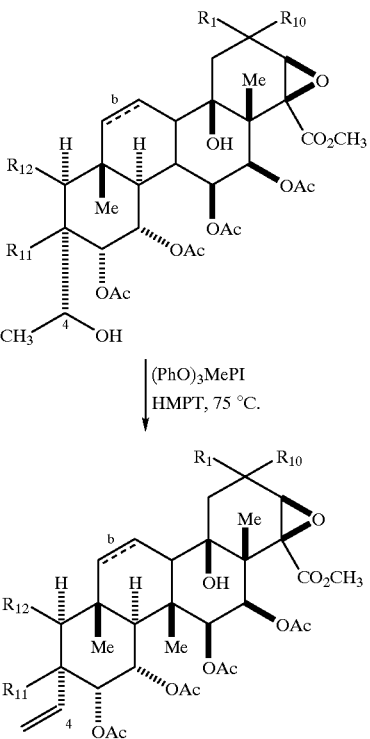

As depicted in Reaction Scheme O, esters at C4 can be prepared by reaction of a preformed carboxylic acid chloride with the C4 alcohol derivative (Reaction Scheme F) in a basic solvent such as pyridine. It should be understood that $R^{4'}$ is used to represent a portion of the $R^4$ definition, e.g. $R^4$ can be an alkyl carbonate which is depicted in the scheme as $OC(=O)OR^{4'}$, $R^{4'}$ representing the alkyl substituent. The acid chlorides, when not purchased, are prepared by stirring the carboxylic acids in reagents such as oxalyl chloride or thionyl chloride. Esters may also be prepared by reaction of the acid chloride and C4 alcohol with silver cyanide (AgCN) in an aprotic solvent such as HMPA. C4 sulfonate derivatives are prepared in a similar manner by reaction with sulfonyl chlorides.

C4 carbonate and carbamate derivatives are prepared by first reacting the C4 alcohol derivative with carbonyldiimidazole (CDI) to obtain the imidazolecarbonyl intermediate which is then reacted with an alcohol or amine ($R^1R^2NH$) to give the corresponding carbonate or carbamate derivatives.

C4 ether derivatives can also be prepared. The best procedure involves reacting an alcohol with trifluoromethanesulfonic anhydride ($Tf_2O$, triflic anhydride) in the presence of a hindered base such as 2,6-di-t-butyl pyridine to obtain the preformed triflate in dichloromethane at reduced temperature, preferably −78° C. To this solution is added the triterpene alcohol, the reaction mixture is warmed to room temperature and stirring is continued until reaction is complete. Ethers may also be prepared by heating a mixture of triterpene C4 alcohol, the appropriate alkylhalide and an excess of silver oxide ($Ag_2O$) in an aprotic inert solvent such as DMF.

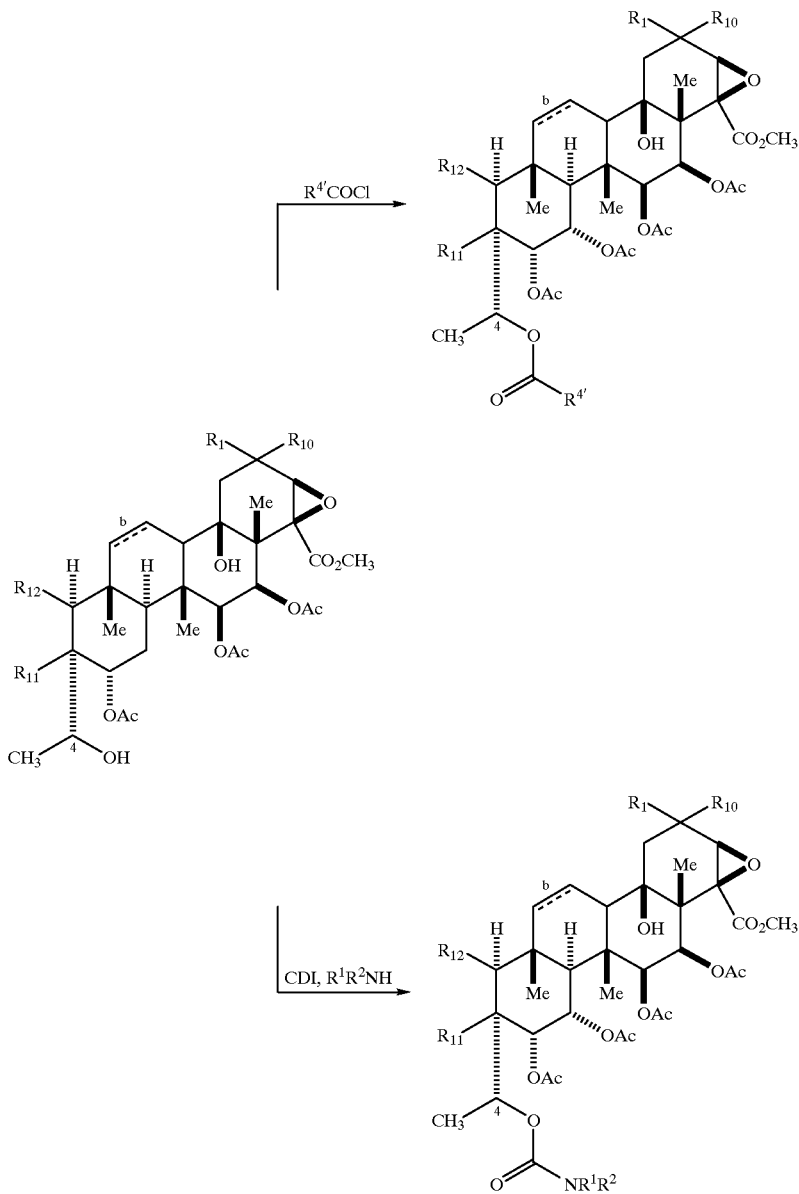

REACTION SCHEME O

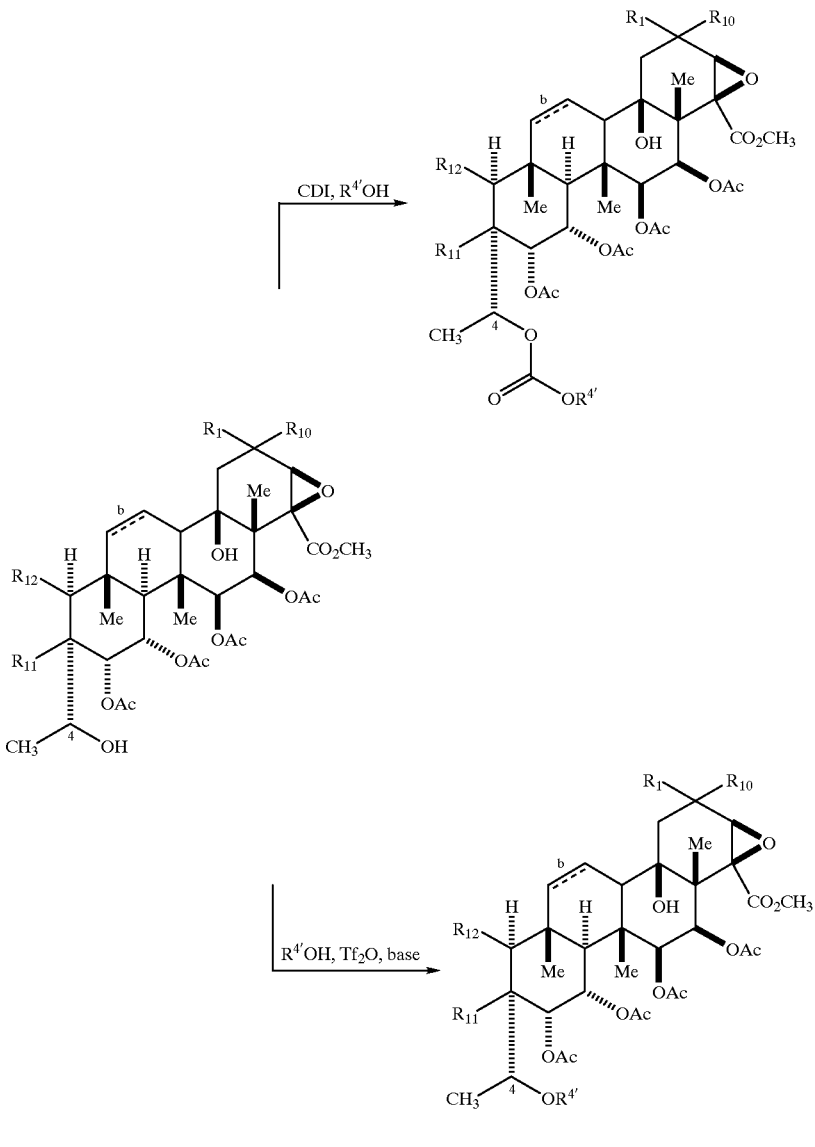

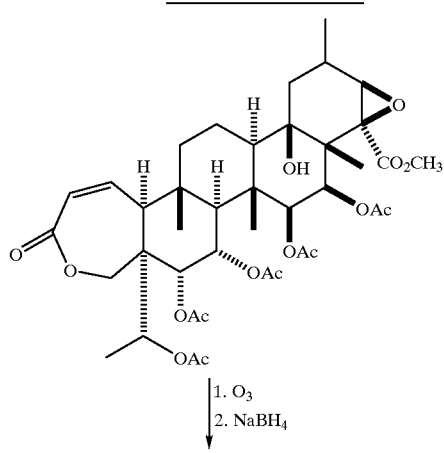

REACTION SCHEME P

The $C_1$–$C_{10}$ bond of Compound 1a can be broken by the following sequence. Firstly, the terminal olefin was reduced by catalytic hydrogenation as described in Reaction Scheme D. Then the A-ring was cleaved by ozonolysis and reductive workup with an agent such as sodium borohydride gives the lactol intermediate. The purified lactol intermediate is then reacted with trimethylsilylthiophenol and a Lewis acid such as borontrifluoride diethyl etherate to give the thioketal analog. The thioketal may be oxidized with reagents such as mCPBA or $NaIO_4$ or $H_5IO_6$ to afford the sulfoxide, which then eliminates to the dihydrofuran during heating in an inert solvent such as xylene at temperatures >140° C. The olefin of the dihydrofuran may be oxidized with reagents such as ozone or $OsO_4$ to afford the corresponding diol, which may be cleaved by reagents such as $H_5IO_6$ to produce the ketone. The formyl ester may be removed by solvolysis with an alcohol and silica gel, and the resulting hydroxy group may be modified using procedures described in Reaction Schemes I, J and O.

27
-continued
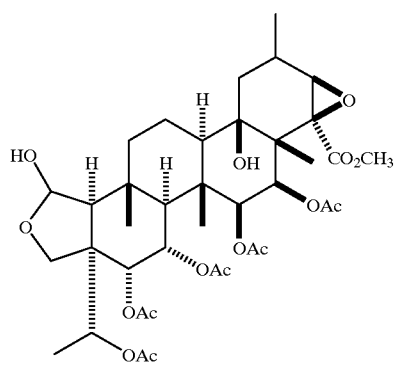
TMS-SPh, BF$_3$·OEt$_2$ ↓
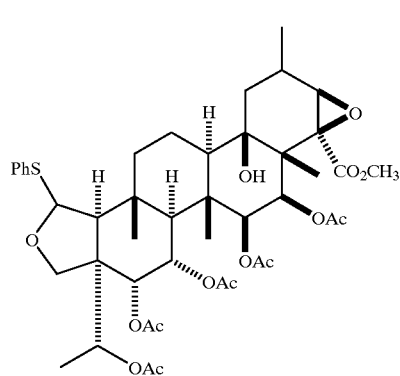
mCPBA ↓
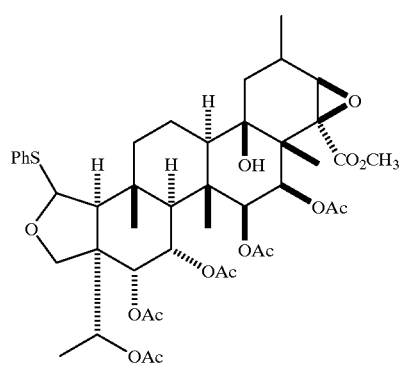
Xylene, 140 °C. ↓
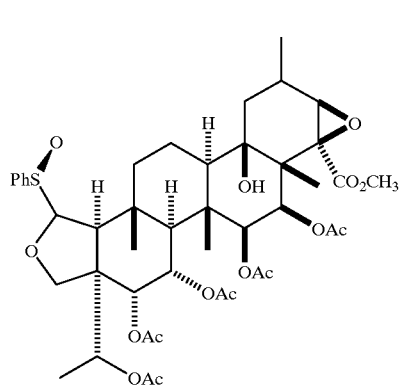
28
-continued
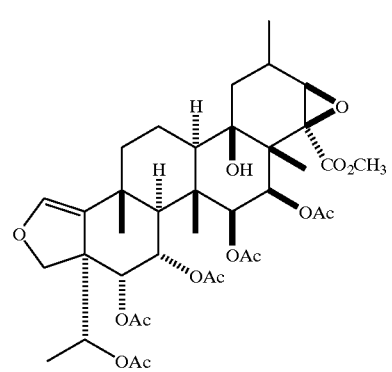
O$_3$, (CH$_3$)$_2$S ↓
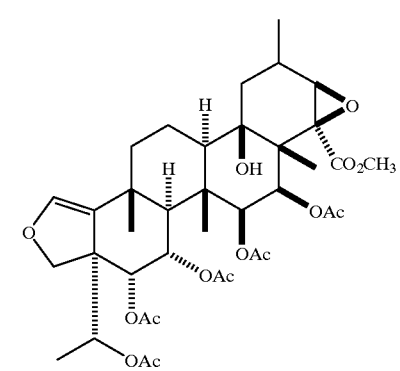
1. O$_3$
2. (CH$_3$)$_2$S ↓
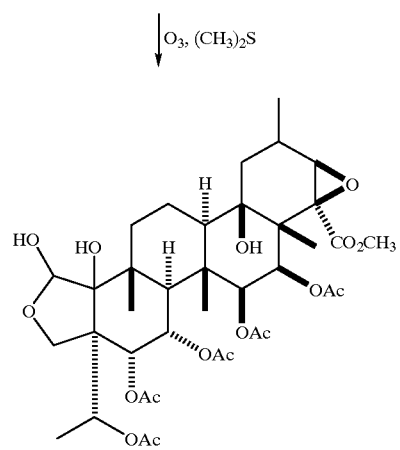
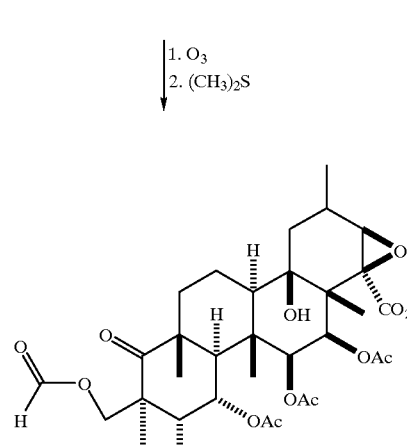

-continued

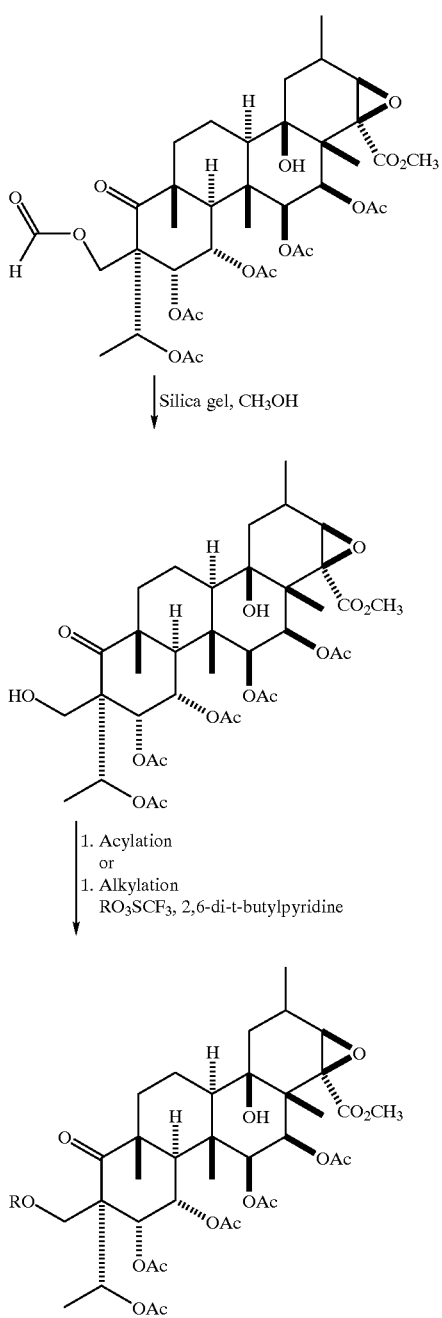

As seen in Reaction Scheme Q, compound Ia [(4,6,7,15, 16-pentakis(acetyloxy)-21,22-epoxy-18-hydroxy-22-methyoxycarbonyl-[6α, 7α, 15β, 16β, 21β, 22β]D:A-Freido-A-homo-27,30-dinor-24-oxaoleana-1, 20(29)-dien-3-one] can be selectively deoxygenated at the C21–C22 epoxide to give the olefin analog. This conversion can be achieved by reaction with a tungsten complex (prepared by the reaction of $WCl_6$ with 3 equivalents of butyllithium in THF at −78° C.) in THF at 55° C. for 12–24h. This olefin analog may then be utilized by the skilled artisan to make the tetracyclic compounds of the instant invention with a double bond at C21–C22.

REACTION SCHEME Q

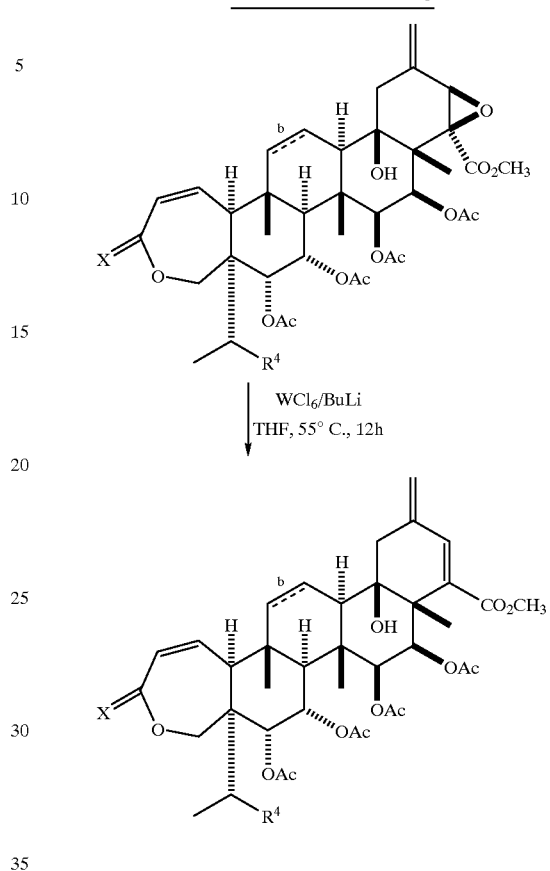

UTILITY

The present invention is related to compounds of formula I, including but not limited to those specified in the examples, which are useful in a mammalian subject for the treatment and prevention of immune mediated diseases such as the resistance by transplantation of organs or tissue such as heart, kidney, liver, medulla ossium, skin, cornea, lung, pancreas, intestinum tenue, limb, muscle, nervus, duodenum, small-bowel, pancreatic-islet-cell, including xeno transplants, etc.; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, and the like; and further infectious diseases caused by pathogenic microorganisms. Further uses may include the treatment and prophylaxis of inflammatory and hyperproliferative skin diseases and cutaneous manifestations of immunologically mediated illnesses, such as psoriasis, atopical dermatitis, contact dermatitis and further eczematous dermatitises and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucous and blood vessels such as gastric ulcers, vascular damage caused by ischemic diseases and thrombosis, ischemic bowel diseases, inflammatory bowel diseases, necrotizing enterocolitis, intestinal lesions associated with thermal burns and leukotriene B4-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastrointestinal tract (e.g. migraine, rhinitis and eczema); renal diseases such as interstitial nephritis, Good-pasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fascitis; periodontal disease such as lesions of gingiva, periodontium, alveolar bone and substantia ossea dentis; nephrotic syndrome such as glomerulonephritis; male pattern alopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on.

Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g. necrosis caused by toxin, viral hepatitis, shock, or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytomegalovirus infection, particularly HCMV infection, and antiinflammatory activity; and The compounds of the present invention may also be used in the treatment of immunodepression or a disorder involving immunodepression, such as AIDS, cancer, senile dementia, trauma (including wound healing, surgery and shock) chronic bacterial infection, and certain central nervous system disorders.

A method of treating a condition in a mammal, the treatment of which is effected or facilitated by Kv1.3 inhibition, comprising the administration, in an amount that is effective at inhibiting $K_v1.3$, of a compound of Formula I. The method of treating a condition in a mammal, the treatment of which is effected or facilitated by $K_v1.3$ inhibition, wherein the condition is selected from the group consisting of: immune mediated diseases such as the resistance by transplantation of organs or tissue such as heart, kidney, liver, medulla ossium, skin, cornea, lung, pancreas, intestinum tenue, limb, muscle, nervus, duodenum, small-bowel, pancreatic-islet-cell, including xeno transplants, etc.; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, and the like; and further infectious diseases caused by pathogenic microorganisms. Further uses may include the treatment and prophylaxis of inflammatory and hyperproliferative skin diseases and cutaneous manifestations of immunologically mediated illnesses, such as psoriasis, atopical dermatitis, contact dermatitis and further eczematous dermatitises and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucous and blood vessels such as gastric ulcers, vascular damage caused by ischemic diseases and thrombosis, ischemic bowel diseases, inflammatory bowel diseases, necrotizing enterocolitis, intestinal lesions associated with thermal burns and leukotriene B4-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastrointestinal tract (e.g. migraine, rhinitis and eczema); renal diseases such as interstitial nephritis, Good-pasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fascitis; periodontal disease such as lesions of gingiva, periodontium, alveolar bone and substantia ossea dentis; nephrotic syndrome such as glomerulonephritis; male pattern aleopreia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-C4 release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g. necrosis caused by toxin, viral hepatitis, shock, or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmention of chemotherapeutic effect, preventing or treating activity of cytomegalovirus infection, particularly HCMV infection, and antiinflammatory activity; and immunodepression or a disorder involving immunodepression, such as AIDS, cancer, senile dementia, trauma (including wound healing, surgery and shock), chronic bacterial infection, and certain central nervous system disorders.

An embodiment of the invention is a method for the treatment of autoimmune diseases. Another embodiment of the invention is a method for the prevention of rejection of foreign organ transplants comprising administering to a patient in need of such treatment a therapeutically effective amount of a compound of formula I.

One end result of an autoimmune or a rejection process is tissue destruction caused by inflammatory cells and the mediators they release. Anti-inflammatory agents such as NSAID's and corticosteroids act principally by blocking the effect or secretion of these mediators, but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immuno-suppressive agents are as likely to succumb from infection as they are from their autoimmune disease.

Cyclosporin A is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting fewer side effects are constantly being searched for in the field. The present invention provides for immunosuppressant agents which are inhibitors of a voltage dependent potassium channel, $K_v1.3$, that is found on human T-lymphocytes.

Potassium channels modulate a number of cellular events such as muscle contraction, neuro-endocrine secretion, frequency and duration of action potentials, electrolyte homeostasis, and resting membrane potential. These channels comprise a family of proteins that have been classified according to their biophysical and pharmacological characteristics. Inhibition of $K^+$ channels, in their role as modulators of the plasma membrane potential in human T-lymphocytes, has been postulated to play a role in eliciting immunosuppressive responses. In regulating membrane potential, $K^+$ channels play a role in the regulation of intracellular $Ca^{++}$ homeostasis, which has been found to be important in T-cell activation. The biochemical characterization of $K^+$ channels is underdeveloped, due to the paucity of selective high affinity probes.

Functional voltage-gated $K^+$ channels can exist as multimeric structures formed by the association of either identical or dissimilar subunits. This phenomena is thought to account for the wide diversity of $K^+$ channels. However, subunit compositions of native $K^+$ channels and the physiologic role that particular channels play are, in most cases, still unclear.

The $K_v1.3$ channel is a voltage-gated potassium channel that is found in neurons, blood cells, osteoclasts and T-lymphocytes. The Chandy and Cahalan laboratories proposed a hypothesis that blocking the $K_v1.3$ channel would elicit an immunosuppressant response. (Chandy et al., *J. Exp. Med.* 160, 369, 1984; Decoursey et al., Nature, 307, 465, 1984). However, the K+ channel blockers employed in their studies were non-selective. Until research with the peptide margatoxin, a peptide found in scorpion venom, no specific inhibitor of the $K_v1.3$ channel existed to test this hypothesis. Although a laboratory (Price et al., *Proc. Natl. Acad. Sci. USA*, 86, 10171, 1989) showed that charybdotoxin would block Kv1.3 in human T cells, charybdotoxin was subsequently shown to inhibit four different $K^+$ channels ($K_v1.3$ and three distinct small conductance $Ca^{++}$ activated $K^+$ channels) in human T-lymphocytes, limiting the use of this toxin as a probe for the physiological role of $K_v1.3$ (Leonard et al., *Proc. Natl. Acad. Sci. USA*, 89, 10094, 1992). Margatoxin, on the other hand, blocks only $K_v1.3$ in T-cells, and has immunosuppressant activity in both in vitro and in vivo models. (Lin et al., *J. Exp. Med*, 177, 637, 1993). Since the compounds of the embodiments of this invention produce blockade of $K_v1.3$, they will also inhibit T-cell activation.

Also within the scope of this invention is a method of treating a condition in a mammal, the treatment of which is effected or facilitated by $K_v1.3$ inhibition, comprising the administration of a pharmaceutical composition comprising a suitable pharmaceutical carrier and a compound of Formula (I), in an amount that is effective at inhibiting $K_v1.3$.

Also within the scope of this invention is a combination therapy comprising a compound of formula I and one or more immunosuppressant agents. These immunosuppressant agents within the scope of this invention include, but are not limited to, IMUREK® azathioprine sodium, brequinar sodium, SPANIDIN® gusperimus trihydrochloride (also known as deoxyspergualin), mizoribine (also known as bredinin), CELLCEPT® mycophenolate mofetil, NEORAL® Cyclosporin A (also marketed as a different formulation of Cyclosporin A under the trademark SANDIMMUNE®), PROGRAF® tacrolimus (also known as FK-506) and RAPIMMUNE® sirolimus (also known as rapamycin), leflunomide (also known as HWA-486), glucocortcoids, such as prednisolone and its derivatives, antibody therapies such as orthoclone (OKT3) and Zenapax and antithymyocyte globulins, such as thymoglobulins.

Using the methodologies described below, representative compounds of the invention were evaluated and found to exhibit $IC_{50}$ values of at least <10 µM in any of the assays thereby demonstrating and confirming the utility of the compounds of the invention as $K_v1.3$ inhibitors and immunosuppressants.

T CELL IL-2 ASSAY

Peripheral blood mononuclear (MNC) cells from healthy donors were separated by density centrifugation with ficoll-hypaque (LSM, Organon Teknika, Durham, N.C.), followed by rosetted with neuraminidase treated sheep red blood cells (SRBC). After another centrifugation with leucocyte separation medium (LSM), the SRBC of the rosetted T cells were then lysed with ammonium chloride lysing buffer (GIBCO, Grand Island, N.Y.). Such purified T cells were resuspended at $3 \times 10^6$/ml in RPMI 1640 culture medium (GIBCO) supplemented with 10% fetal calf serum (Sigma, St. Louis, Mo.), 100 mM glutamine, 1 mM sodium pyruvate, 0.1 mM non-essential amino acids, and 1% penn-strep (GIBCO). The cell suspension was immediately distributed into 96 well round-bottom microculture plates (Costar) at 200 µl/well. The various dilutions of test compound were then added in triplicate wells at 25 µl/well, incubated for 30 min at 37° C. Ionomycin (125 ng/ml), and PMA (1 or 5 ng/ml), were added to the appropriate wells. The culture plates were then incubated at 37° C. in a humidified atmosphere of 5% $CO_2$-95% air for 18–24 hours. The supernatants were removed, and assayed for IL-2 with an IL-2 capture ELISA, using monoclonal anti-IL-2, and biotinylated goat anti-IL-2 antibodies (unconjugated antibodies purchased from R&D System, Minneapolis, Minn.). The ELISA was developed with streptavidin conjugated peroxidase (Zymed, San Francisco, Calif.) and substrate for peroxidase (Sigma). Mean OD and units of IL-2 of the replicate wells were calculated from standard curve, created with recombinant IL-2 (Collaborative Biomedical Products, Bedford, Mass.) and the results were expressed as concentration of compound required to inhibit IL-2 production of T cells by 50%.

T CELL PROLIFERATION ASSAY

Peripheral blood mononuclear cells (MNC) from healthy donors were separated by density centrifugation with ficoll-hypaque (LSM, Organon Teknika, Durham, N.C.). After washing the MNC with complete media (RPMI 1640 medium with 5% fetal calf serum, 100 mM glutamine, 1 mM sodium pyruvate, 0.1 mM non-essential amino acid, and 1% penn-strep, obtained from GIBCO, Grand Island, N.Y.), they were then irradiated at 7500 RADS, and resuspended at $4$–$4.5 \times 10^6$ cells/ml in complete media. Another aliquot of MNC were rosetted with neuraminidase treated SRBC. After another centrifugation with LSM, the sheep red blood cells (SRBC) of these rosetted T cells were then lysed with ammonium chloride lysing buffer (GIBCO, Grand Island, NY). After washing 2x with complete media, these purified T cells were also resuspended at $2$–$2.5 \times 10^6$ cells/ml in complete media. The various dilutions of the compound were added in triplicates at 50 ul/well of a 96 well flat-bottom microculture plate (Costar, Cambridge, Mass.). T cell suspension was then immediately distributed into the wells at 100 ul/well. After incubating the cells with compound for 30 min. at 37° C. in a humidified atmosphere of 5% $CO_2$-95% air, 20 µl/well of anti-CD3 (Ortho Diagnostic, N.J.) at final conc. of 0.3 ng/ml was added, followed by 50 µl of the irradiated MNC. The culture plates were then incubated at 37° C. in a humidified atmosphere of 5% $CO_2$-95% air for 72 hours. The proliferation of T lymphocytes was assessed by measurement of tritiated thymidine incorporation. During the last 18–24 hrs. of culturing, the cells were pulse-labeled with 2 µCi/well of tritiated thymidine (NEN, Cambridge, Mass.). The cultures were harvested on glass fiber filters using a multiple sample harvester (MACH-II, Wallac, Gaithersburg, Md.). Radioactivity of filter discs corresponding to individual wells was measured by standard liquid scintillation counting methods (Betaplate Scint Counter, Wallac). Mean counts per minute of replicate wells were calculated and the results were expressed as concentration of compound required to inhibit tritiated thymidine uptake of T cells by 50%.

KV1.3-RUBIDIUM EFFLUX ASSAY

CHO cells transfected with $K_v1.3$ channels at site densities of approximately 40,000 sites/cell are plated into 96 well culture plates and maintained in Iscove's Modified Dulbecco's Medium (IMDM, with L-Glutamine and HEPES, JRH Biosciences). Cells are incubated overnight with $^{86}Rb^+$ (3 µCi/ml, Dupont-NEN) in the glutamine supplemented IMDM. After aspiration of the media, 100 µl of Low K Buffer (in mM, 6.5 KCl, 125 NaCl, 1 $CaCl_2$, 2 $MgCl_2$, 10 HEPES, pH adjusted to 7.2 with NaOH) is added to each well followed by 100 µl test samples in Low K Buffer also containing 0.2% BSA and 2 mM ouabain.

Samples are tested at either 1 μg/ml for routine screening or at a variety of concentrations encompassing at least 1/10 to 10 times the putative $IC_{50}$ of test compound to determine potency. After a fixed preincubation time, which is usually 10 min, the samples are aspirated. The $K_v1.3$ channels are opened by depolarization of the cells with High K Buffer (final concentrations, in mM, 63.25 KCl, 68.25 NaCl, 1 $CaCl_2$, 2 $MgCl_2$, HEPES, pH adjusted to 7.2 with NaOH) also containing test compounds. To measure $^{86}Rb^+$ efflux through the channels, aliquots of 100 μl are taken from each well after a given time and added to plates containing 100 μl MicroScint-40 (Packard) for counting by liquid scintillation techniques. MicroScint-40 (100 μl) is then added to each well of the cell plate to determine the remaining $^{86}Rb^+$ activity. The efflux counts are normalized for the total amount of $^{86}Rb^+$ that was in the cells by adding the efflux counts to the cell plate counts. Activity is determined by % inhibition of the efflux window that is established using a saturating concentration of margatoxin (MgTX), a 39 amino acid peptide that is a potent blocker of $K_v1.3$ channels ($IC_{50}$=100 pM).

DOSAGE FORMS

As an immunosuppressive, these compounds are useful in the treatment of autoimmune diseases, the prevention of rejection of foreign organ transplants and/or related afflictions, diseases and illnesses.

The compounds of this invention can be administered for the treatment of autoimmune diseases, the prevention of rejection of foreign organ transplants and/or related afflictions, diseases and illnesses according to the invention by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1–500 milligrams per day. Ordinarily, from 10 to 100 milligrams per day in one or more applications is effective to obtain desired results. These dosages are the effective amounts for the treatment of autoimmune diseases, the prevention of rejection of foreign organ transplants and/or related afflictions, diseases and illnesses.

The active ingredient can be administered orally in solid dosage forms, such as capsules, tablets, troches, dragees, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention can be illustrated as follows:

CAPSULES

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

SOFT GELATIN CAPSULES

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol. The solution is made to volume with water for injection and sterilized.

SUSPENSION

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

The following examples illustrate the preparation of the compounds of Formula I and as such are not to be considered as limiting the invention set forth in the claims appended hereto.

EXAMPLE 1

A Method Of Extracting The Compounds Of Formula 1(a) and 1(b) From *Spachea correa*

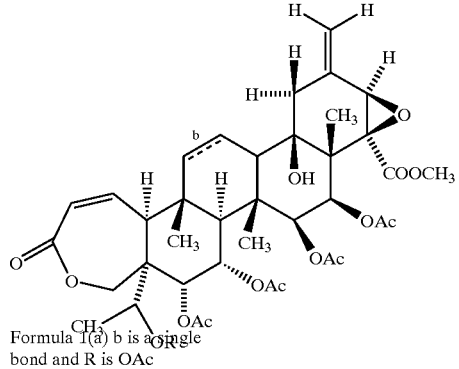

Formula 1(a) b is a single bond and R is OAc

Formula 1(b) b is a double bond and R is OAc

One gram of an ethanol extract of the roots of *Spachea correa* was partitioned between 100 ml of hexane (twice) and 100 ml of 90% aqueous methanol. After separation of the phases, the defatted methanol was concentrated down under vacuum to give an aqueous suspension. This was diluted out to 100 ml with water and extracted, with 100 ml of methylene chloride.

The bioactive methylene chloride extract was dried down to give 12 mg of residue. This was first fractionated by preparative thin layer chromatography (TLC) on a 20 cm by 20 cm E. Merck silica gel 60$F_{254}$ plate of 1 mm thickness using methylene chloride-ethyl acetate 1:1 (v/v) as solvent, then by high performance liquid chromatography (HPLC) using a ZORBAX Rx$C_8$ 4.6 mm×25 cm column, operated at 50° C. and eluted with a 50 minute gradient of acetonitrile-:water (1:1, v/v) to 100% acetonitrile, delivered at 1 m/min, to afford compounds 1(a) and 1 g 1(b).

Homogeneity of the preparations was ascertained in several TLC systems, such as E. Merck silica gel 60$F_{254}$, methylene chloride-ethyl acetate 1:1, Rf 1(a) 0.4, Rf 1(b) 0.3; Whatman K$C_{18}$, methanol-water 9:1, Rf 1(a) 0.65, Rf 1(b) 0.75 and by HPLC using a ZORBAX Rx$C_8$ column, acetonitrile-water 3:2, k'1(a) 4.15, k'1(b) 3.30; and by NMR.

Mass spectra were recorded on JEOL SX-102A (electron impact, EI,903V) and JEOL HX110 (Fast Atom Bombardment, FAB) mass spectrometers. Exact mass measurements were performed at high resolution (HR-EI) using perfluorokerosene (PFK) as the internal standard. Trimethylsilyl derivatives were prepared with a 1:1 mixture of BSTFA-pyridine at room temperature The FAB spectrum was run in a matrix of dithiothreitol (20/80).

The compound of Formula 1(a) runs underivatized by EI. The molecular ion is observed a m/z 788 and three successive loses of acetic acid are observed. The base peak is observed a m/z 334. The compound does not silylate. Scanning HR-EI indicated a molecular formula of $C_{40}H_{52}O_{16}$. A table of the critical HR-EI data is given below.

| Observed m/z | Formula | Assignment |
|---|---|---|
| 788.3220 | $C_{40}H_{52}O_{16}$ | M + |
| 728.3040 | $C_{38}H_{48}O_{14}$ | M-acetic acid |
| 668.2834 | $C_{36}H_{44}O_{12}$ | M-2 × acetic acid |
| 334.1417 | $C_{18}H_{22}O_6$ | base peak |

$^{13}$C NMR spectra were recorded for the compound of Formula 1(a) in $CD_2Cl_2$ at 100 MHz on a Varian Unity 400 NMR spectrometer at 20° C. Chemical shifts are given in ppm relative to tetramethylsilane (TMS) at zero ppm using the solvent peak at 53.8 ppm as internal standard. The following data were observed: 15.0, 15.2, 16.8, 17.1, 20.7*, 20.9, 21.1, 21.6, 21.8, 22.2, 35.6, 40.8*, 42.1, 43.6, 45.1, 47.5, 49.3*, 53.5, 59.1, 62.6, 63.5, 66.1, 66.7*, 68.4*, 69.9, 73.9, 75.0, 75.6, 77.1*, 119.4, 123.7, 138.9, 143.0, 167.7, 169.2, 169.3*, 170.25, 170.31, 170.8, 171.3 ppm (where the * signifies the observation as broad resonances). The carbon count of 40 is in agreement with the molecular formula $C_{40}H_{52}O_{16}$ derived by scanning HR EI-MS.

The $^1$H NMR spectra of compound of Formula(a) was recorded at 400 MHz in $CD_2Cl_2$ on a Varian Unity 400 NMR spectrometer at 25° C. Chemical shifts are in ppm relative to TMS at zero ppm using the solvent peak at δ5.32 as the internal standard.

The mass spectra of the compound of Formula 1(b) was obtained as above. The following results were obtained.

| Observed m/z | Formula | Assignment |
|---|---|---|
| 786.3075 | $C_{40}H_{50}O_{16}$ | M + |
| 726.2886 | $C_{38}H_{46}O_{14}$ | M-acetic acid |
| 666.2651 | $C_{36}H_{42}O_{12}$ | M-2 × acetic acid |
| 606.2451 | $C_{34}H_{38}O_{10}$ | M-3 × acetic acid |
| 489.2099 | $C_{26}H_{33}O_9$ | base peak |
| 471.1992 | $C_{26}H_{31}O_8$ | |

$^{13}$C NMR spectra were recorded for the compound of Formula1(b) using the procedure described above. The following results were observed: 14.8, 14.9, 17.3, 20.8, 20.9, 21.3, 21.7, 21.8, 21.9, 27.1, 35.1, 40.6, 42.3, 45.4, 48.1, 50.4, 53.5, 54.1, 57.8, 63.7, 66.2, 67.8, 68.6, 71.4, 73.3, 73.8, 74.4, 119.5, 121.1, 124.3, 137.1, 138.9, 143.3, 167.6, 168.6, 169.3, 169.5, 169.9, 171.0, 171.7 ppm.

The carbon count of 40 is in agreement with the molecular formula $C_{40}H_{50}O_{16}$ derived by scanning HR El-MS.

EXAMPLE 2

A Method Of Extracting The Compounds Of Formula 1(c) And 1(d) From *Spachea Correa*

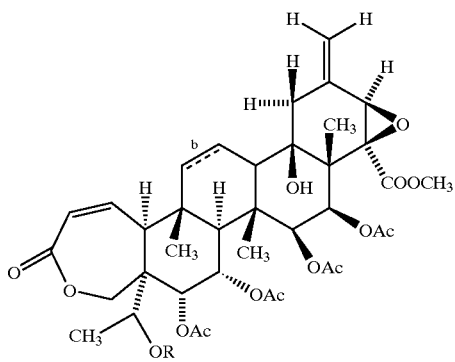

Formula 1(c) b is a single bond and R is OH

Formula 1(d) b is a double bond and R is OH

Analogs of the compounds of Formula 1(a) and 1(b) could be detected in the crude extract and fractions thereof when the process of Example 1 was carried out on a larger scale. Thus, 50 g of ethanol extract were partitioned as described in Example 1 using 900 ml of each solvent at each step.

Partial purification of the methylene chloride extract was achieved by column chromatography on E. Merck silica gel 60 (120 ml), eluting with a step gradient of ethyl acetate in methylene chloride. The step gradient was designed so that the column was washed first with 100% methylene chloride and then with methylene chloride-ethyl acetate mixtures of 9:1, 8:2, 3:2, 2:1, 1:1, 1:2, 2:8 and 1:9. Ultimately the column was washed with 100% ethyl acetate. Fractions eluted with methylene chloride-ethyl acetate 3:2 were enriched in compound of Formula 1(a) and 1(b). These were resolved by HPLC using a ZORBAX $RxC_8$ 9 mm×25 cm column, maintained at 50° C. and eluted at 4 ml/min with acetonitrile-water 1:1 v/v. Three identical runs finally afforded 1(a) and 1(b) after crystallization from methanol. Later-eluting fractions from the silica gel column above were found to contain at least two related compounds based on UV spectra and color reactions on TLC plates. Material from the methylene chloride-ethyl actate 1:1 and 1:2 washings were combined and evaporated down. Separation was achieved on the same HPLC column as above, eluting with a 50 minute gradient of 30% to 50% acetonitrile in water. Two identical runs gave purified compound 1(c). Fractions containing the compound of Formula 1(d) were again processed by HPLC (same column) using acetonitrile-water 3:7 delivered isocratically, to yield the purified compound of Formula 1(d).

The mass spectra of these compounds were recorded on a Finnigan TSQ700 mass spectrometer (electrospray ionization, ESI). The samples were analyzed by LC/MS using a 2.1×150 mm $C_8$ column at 0.2 ml/min. with a mobile phase of 45% acetonitrile/0.01M aqueous ammonium acetate at 50° C. Component 1(d) had a retention time of 10.5 min. and a molecular weight of 744 which is observed a m/z: 745 (M+H), 762 (M+NH$_3$), 786 (M+H+MeCN). Component 1(c) has a retention time of 11.8 min. and a molecular weight of 746 which is observed at m/z: 747 (M+H), 764 (M+NH$_3$) and 788 (M+H+MeCN).

The $^{13}$C NMR spectra obtained for the compound of Formula 1(c) using the conditions previously described is as follows: 15.1 (2x), 16.9, 19.8, 20.8, 20.91, 20.94, 21.9, 22.3, 35.6, 40.6, 42.2, 43.9, 45.0, 47.7, 50.8, 53.5, 55.6, 61.8, 63.5, 66.0, 67.6 (2x), 69.8, 70.0, 73.9, 75.0, 75.6, 119.3, 123.7, 139.0, 144.4, 167.8, 169.2, 169.5, 170.1, 170.4, 171.4 ppm.

The carbon count of 38 is in agreement with the molecular formula $C_{38}H_{50}O_{16}$ derived by scanning HR EI-MS.

EXAMPLE 3

Separation By HPLC

Compounds of this invention were characterized by the following behavior during HPLC separation on a ZORBAX $RxC_8$ 4.6 mm×25 cm column, maintained at 50° C. and eluted at 1 ml/min with acetonitrile-water 3:2 v/v): Compound 1(a): k'=4.15; 1(b): k'=3.30; 1(c): k'=2.30; 1(d): k'=2.10.

Analyses using this HPLC system can be used to quantify the compounds in the crude extract or other mixtures, by comparing the absorbance of HPLC peaks at a wavelength of 220 nm with that produced by injections of known (weighed) amounts of pure standards.

EXAMPLE 4

Additional Purification Procedure

A simplified purification process allows for rapid fractionation of even larger amounts of crude extract and the preparation of gram amounts of the compounds of Formula 1(a) and 1(b).

The ethanol extract is first dissolved at 20 grams per 150 ml in methanol. This solution is diluted with 150 ml of water and then extracted three times with methylene chloride using 150 ml of methylene chloride each time. The pooled methylene chloride extracts are evaporated down and fractionation proceeds by repeated column chromatography on silica gel. One employs methylene chloride-methanol 97:3 in a first step; the mixed compounds of Formula 1(a) and 1(b) thus obtained are resolved by chromatographing on fresh silica gel eluted with methylene chloride-ethyl acetate 3:1. Volume of elution for the compound of Formula 1(a) ranges from about 2 to about 3.5 column volumes of solvent; that for the compound of Formula 1(b) is about 3 to about 4.5 column volumes. Finally, advantage is taken of the low solubility of these compounds, and, after total resolution by chromatography, the compounds of Formula 1(a) and 1(b) can be precipitated and or crystallized from concentrated methanol solutions.

EXAMPLE 5

4,6,7,15,16-Pentakis(acetyloxy)-21,22-epoxy-18-hydroxy-22-methoxycarbonyl-D:A-Friedo-A-homo-27,30-dinor-24-oxaoleana-1,20(29)-diene

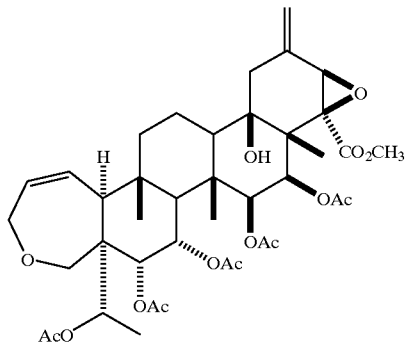

Step A: 4,6,7,15,16-pentakis(acetyloxy)-21,22-epoxy-18-hydroxy-22-methoxycarbonyl-D:A-Friedo-A-homo-27,30-dinor-24-oxaoleana-1,20(29)-dien-3-ol A solution of 3.0 g (3.8 mmole) of 4,6,7,15,16-pentakis(acetyloxy)-21,22-epoxy-18-hydroxy-22-methoxycarbonyl-D:A-Friedo-A-homo-27,30-dinor-24-oxaoleana-1,20(29)-dien-3-one in 20 mL of dry dichloromethane was cooled to 0° C. under nitrogen. Then 9 mL of a 1M solution of lithium tri-(tert-butoxy)aluminum hydride was added dropwise and the solution was stirred at 0° C. After 18 h, the reaction was quenched by dropwise addition of 20 mL of 2M aqueous $H_2SO_4$ and the mixture was diluted with 200 mL of ether. The layers were separated and the aqueous layer was washed with two 100 mL portions of ether. The organic layers were sequentially washed with 20 mL of 2M aqueous $H_2SO_4$ and brine, then were combined, dried over $MgSO_4$, and concentrated to afford the title compound, which was used directly in the next step.

Step B: 4,6,7,15,16-Pentakis(acetyloxy)-21,22-epoxy-18-hydroxy-22-methoxycarbonyl-D:A-Friedo-A-homo-27,30-dinor-24-oxaoleana-1,20(29)-diene A sample of 2.9 g of crude 4,6,7,15,16-pentakis(acetyloxy)-21,22-epoxy-18-hydroxy-22-methoxycarbonyl-D:A-Friedo-A-homo-27,30-dinor-24-oxaoleana-1,20(29)-dien-3-ol was dissolved in 10 mL of dry dichloromethane under nitrogen. To this was added 10 mL of triethyl-silane, and the solution was stirred at room temperature for 10 min. Then 2 mL (20 mmole) of boron trifluoride etherate was added and the mixture was stirred at room temperature for 15 min. The reaction was quenched by addition of 10 mL of saturated aqueous $KHCO_3$ solution and the resulting mixture was partitioned between ether and water. The water layer was washed with ether and the organic extracts were washed with brine, then were combined, dried over $MgSO_4$, and concentrated. The residue was purified by chromatography on silica gel using 30% ethyl acetate-hexane to afford the title compound. $^1H$ NMR ($CDCl_3$) δ4.14, 4.34 (dd, AB, 2H, J=12 Hz, C3-H); Mass Spectrum (APCI) m/e 792 ($M^+NH_4$).

EXAMPLE 6

4,6,7,15,16-Pentakis(acetyloxy)-21,22-epoxy-18-hydroxy-22-methoxycarbonyl-D:A-Friedo-A-homo-27,30-dinor-24-oxaoleana-1-en-3-one

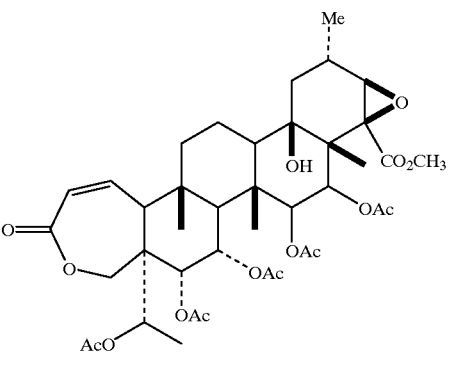

A solution of 50mg (63.7 μmole) of 4,6,7,15,16-Pentakis(acetyloxy)-21,22-epoxy-18-hydroxy-22-methoxycarbonyl-D:A-Friedo-A-homo-27,30-dinor-24-oxaoleana-1,20(29)-dien-3-one in 50 ml of dry THF was degassed under reduced pressure and saturated with nitrogen, the procedure being repeated several times. 25mg of Wilkinson's catalyst [$(PPh_3)_3RhCl$] were added and the solution was degassed and saturated with hydrogen in the previously described manner. The reaction vessel was now pressurized with $H_2$ to 15 psi (1 atm) and shaken for 65 h at 25° C. After that time the solvent was removed under reduced pressure. The residue was dissolved in a small amount of ethyl acetate/hexanes (2:1) (ca. 1 mL) and filtered through 30 g of silica gel eluting with 500ml of ethyl acetate/hexanes (2:1). The first fractions, containing the Wilkinson-catalyst (approx. 50mL) were discarded. The fractions containing the product were combined. After removing the solvent under reduced pressure the crude product was dried in vacuo and purified by HPLC to afford the title compound. $^1H$ NMR ($CDCl_3$) δ1.5 (d, 3H, J=8.6 Hz, C29-H), 2.4 (m, 1H, C20-H); Mass Spectrum (APCI): m/e 808.

EXAMPLE 7

4,6,7,15, 16-Pentakis(acetyloxy)-20,21,22,29-diepoxy-18-hydroxy-22-methoxycarbonyl-D:A-Friedo-A-homo-27,30-dinor-24-oxaoleana-1,20(29)-en-3-one

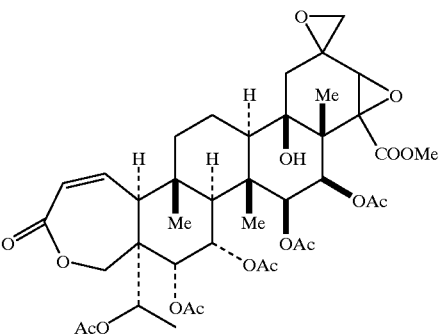

A solution of 50 mg of 4,6,7,15,16-pentakis(acetyloxy)-21,22-epoxy-18-hydroxy-22-methoxycarbonyl-D:A-Friedo-A-homo-27,30-dinor-24-oxaoleana-1,20(29)-dien-3-one (0.05 mmole) and 150 mg of m-chloro perbenzoic acid (80–85%; remainder water; 0.7 mmole) in 5 ml of $CHCl_3$ was stored at 0° C. for 21 days. The solution was diluted with 50 ml of dichloromethane, 20 ml of a saturated aqueous solution of $NaHCO_3$ was added and the layers were separated. The organic layer was consecutively washed with 20 mL of 1M hydrochloric acid and saturated aqueous sodium chloride then was dried over MgSO$_4$ and concentrated. The residue was purified by silica gel chromatography with 1:1 ethyl acetate-hexane to afford the title compound. $^1$H NMR (CDCl$_3$) δ2.92, 3.21 (AB, 2H, J=4.0 Hz, C29-H), 3.30 (s, 1H, C21-H), 6.09 (d, 1H, J=11.9 Hz, C2-H), 6.33 (dd, 1H, J$_1$=11.9 Hz, J$_2$=8.9 Hz, C1-H); $^{13}$C NMR (CDCl$_3$) δ123.5 (C-2), 142.3 (C-1); Mass Spectrum (APCI): m/e 822 (M+NH$_4$).

EXAMPLE 8

4,6,7,15,16-pentakis(acetyloxy)-21,22-epoxy-18-hydroxy-22-methoxycarbonyl-D:A-Friedo-A-homo-27,30-dinor-24-oxaoleana-3-one

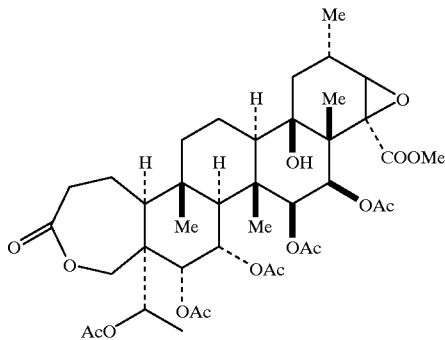

A sample of 25 mg of 4,6,7,15,16-pentakis(acetyloxy)-21,22-epoxy-18-hydroxy-22-methoxycarbonyl-D:A-Friedo-A-homo-27,30-dinor-24-oxaoleana-1-en-3-one (0.03 mmole) was dissolved in 10 ml of methanol. 20 mg of Pd/charcoal (10% Pd) were added and the mixture was hydrogenated on a Parr-apparatus at 25 psi for 14 h at 25° C. After that time the catalyst was filtered off and the solution was concentrated. The residue was first filtered through a plug of silica gel and then purified by HPLC (Waters RCM, μ Porosil, 10 mm×10 cm) using a mixture of 8:4:1 hexane-methyl tert-butyl ether-acetonitrile to afford the title compound.

$^1$H NMR (CDCl$_3$) δ2.48 (d, 3H, J=7.9 Hz, C29-H), 2.37 (m, 1H, C20-H), 2.63–2.71 (m, 1H, C2-H), 2.98 (dt, 1H, J$_1$=18.3 Hz, J$_2$=5.2 Hz, C2-H); Mass Spectrum (APCI): m/e 810 (M+NH$_4$).

EXAMPLE 9

4,6,7,15,16-Pentakis(acetyloxy)-21,22-epoxy-18-hydroxy-22-methoxycarbonyl-D:A-Friedo-A-homo-27,30-dinor-24-oxaoleana-1-en-3,20-dione

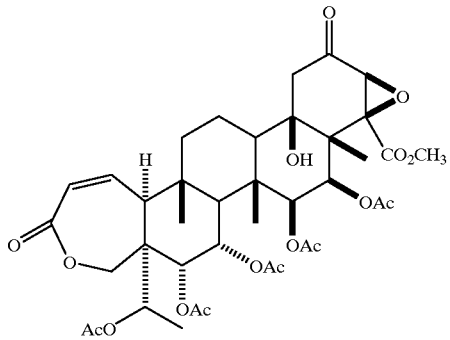

A solution of 13.7 mg of 4,6,7,15,16-Pentakis(acetyloxy)-21,22-epoxy-18-hydroxy-22-methoxycarbonyl-D:A-Friedo-A-homo-27,30-dinor-24-oxaoleana-1,20(29)-dien-3-one in 12 ml of (1:1, CH$_2$Cl$_2$/CH3OH) was cooled to −78° C. and O$_3$ was bubbled into the solution until it contained a blue color. The solution was then purged with nitrogen for 3 minutes and 3 drops of Me$_2$S was added. The solution was allowed to warm to 25° C. for 14 hours. Volitiles were removed by vacuum and the residue was purified by chromatography on silica gel using 25% ethyl acetate-hexane to afford the title compound.

$^1$H NMR (CDCl$_3$) δ2.83 (d, 1H, J=14 Hz), 2.39 (d, 1H, J=14 Hz); Mass Spectrum (EI) m/e 813 (M+Na).

EXAMPLE 10

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-7-hydroxymethyl-6-(3-methoxy-3-oxopropyl)-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene

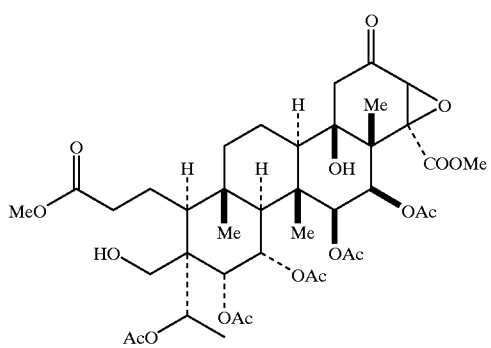

A sample of 12.4 mg of 4,6,7,15,16-pentakis(acetyloxy)-21,22-epoxy-18-hydroxy-22-methoxycarbonyl-D:A-Friedo-A-homo-27,30-dinor-24-oxaoleana-1-en-3,20-dione (0.03 mmole) was dissolved in 5 ml of methanol. Then 11 mg of Pd/charcoal (10% Pd) were added and the mixture was hydrogenated on a Parr-apparatus at 50 psi for 18 h at 25° C. After that time the catalyst was filtered off and the solution was concentrated. The residue was first filtered through a plug of silica gel and then purified by flash chromatography on silica gel using a mixture of 1:1 ethyl acetate-hexane followed by 2:1 ethyl acetate-hexane to afford the title compound.

$^1$H NMR (CDCl$_3$) δ2.83 (d, 1H, J=14 Hz), 2.39 (d, 1H, J=14 Hz), 3.75 (s, 3H. OCH$_3$), 4.0 (s, 3H. OCH$_3$); Mass Spectrum (APCI): m/e 842 (M+NH$_4$).

EXAMPLE 11

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-7-hydroxymethyl-6-(3-methoxy-3-oxopropenyl)-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene

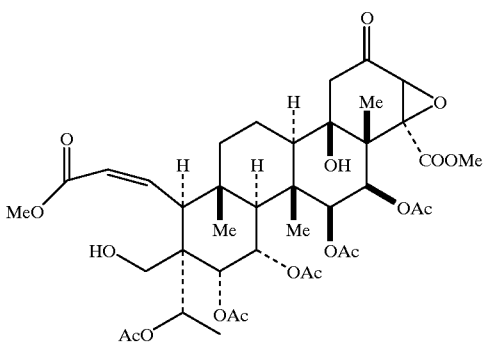

A sample of 700 mg of 4,6,7,15,16-pentakis(acetyloxy)-21,22-epoxy-18-hydroxy-22-methoxycarbonyl-D:A-Friedo-A-homo-27,30-dinor-24-oxaoleana-1-en-3, 20-dione (0.03 mmole) was dissolved in 28 ml of dry tetrahydrofuran and cooled to 0° C. Then a solution of 147.3 mg of LiOH.H$_2$O and 0.4 mL of 30% H$_2$O$_2$ in 7 mL of H$_2$O was added dropwise and the solution was stirred at 0° C. for 90 min. The mixture was partitioned between ethyl acetate and saturated NaHCO$_3$ solution and the aqueous layer was washed with three portions of ethyl acetate. Then the aqueous layer was acidified with 2M HCl and washed with three portions of ethyl acetate. The latter organic extracts were combined, dried over MgSO$_4$, and concentrated. The oily residue was dissolved in ether and treated with an ethereal solution of diazomethane. The excess diazomethane was destroyed by addition of acetic acid and the solution was concentrated. The oily residue was purified by HPLC (Waters RCM, μ Porosil, 25 mm×10 cm) using a mixture of 4:3:1 hexane-methyl tert-butyl ether-acetonitrile to afford the title compound.

$^1$H NMR (CDCl$_3$) δ3.75 (s, 3H. OCH$_3$), 3.95 (s, 3H. OCH$_3$), 6.06 (d, J=7 Hz), 6.63 (t, J=7 Hz). Mass Spectrum (APCI): m/e 842 (M+NH$_4$).

EXAMPLE 12

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6, 7-bis-(hydroxymethyl)-1 1b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydro-cryseno[1,2-b]oxirene

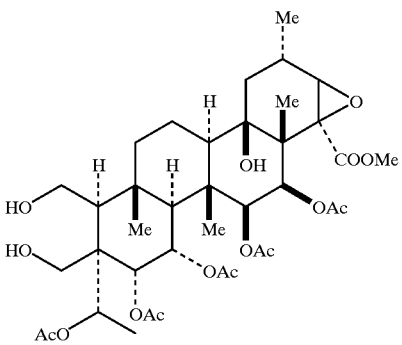

A solution of 80 mg of 4,6,7,5,16-Pentakis(acetyloxy)-21,22-epoxy-18-hydroxy-22-methoxycarbonyl-D:A-Friedo-A-homo-27,30-dinor-24-oxaoleana-1-en-3-one in 10 mL of CH$_2$Cl$_2$ and 10 mL of methanol was cooled to −78° C. and a stream of ozone was passed through it until it turned blue. The solution was then allowed to warm to −20° C. and the stream of ozone was continued for 30 min. After the solution was purged with nitrogen, it was allowed to warm to room temperature and 100 mg of NaBH$_4$ was added. After 15 min, the reaction was quenched with 50 mL of 1M HCl and the mixture was diluted with CH$_2$Cl$_2$. The layers were separated and the aqueous layer was washed with three portions of CH$_2$Cl$_2$. The organic extracts were combined, dried over MgSO$_4$, and concentrated. The oily residue was purified by flash chromatography (silica gel) using 1:1 ethyl acetate-petroleum ether to afford the title compound.

$^1$H NMR (CDCl$_3$) δ3.75 (s, 3H. OCH$_3$), 3.55, 4.02 (AB, 2H, J=12.4 Hz, CH$_2$OH), 4.14 (ABX, 2H, J$_{AB}$=11.9 Hz, J$_{AX}$=1.0 Hz, J$_{BX}$=4.0 Hz, CH$_2$OH); Mass Spectrum (APCI): m/e 786 (M+NH$_4$).

EXAMPLE 13

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-2-epoxymethylidene-3a-hydroxy-6, 7-bis-(hydroxymethyl)-11b-methoxycarbonyl-8, 9, 10, 11-tetraacetoxy-5a, 9b, 11a-trimethyl-1a, 3, 3a, 3b, 4, 5, 5a, 6, 7, 8, 9, 9a, 9b, 10, 11, 11a, 11b-hexadecahydrocryseno[1,2-b]oxirene

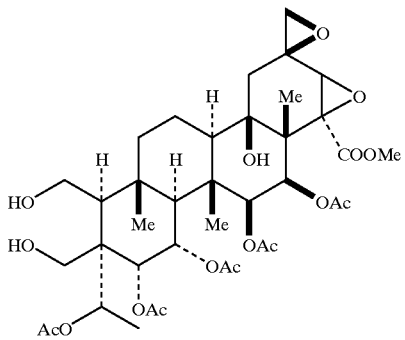

A solution of 400 mg of 4,6,7,15,16-pentakis(acetyloxy)-20,21,22,29-diepoxy-18-hydroxy-22-methoxycarbonyl-D:A-Friedo-A-homo-27,30-dinor-24-oxaoleana-1,20(29)-en-3-one in 10 mL of CH$_2$Cl$_2$ and 10 mL of methanol was cooled to 0° C. and a stream of ozone was passed through it for 90 min. After the solution was purged with nitrogen, it was allowed to warm to room temperature and 400 mg of NaBH$_4$ was added. After 45 min, the reaction was quenched with 20 mL of 1M HCl and the mixture was diluted with CH$_2$Cl$_2$. The layers were separated and the aqueous layer was washed with three portions of CH$_2$Cl$_2$. The organic extracts were combined, dried over Na$_2$SO$_4$, and concentrated. The oily residue was purified by flash chromatography (silica gel) using 4:1 ethyl acetate-hexane to afford the title compound.

$^1$H NMR (CDCl$_3$) δ3.55, (m, 1H, CH$_2$OH), 3.75 (s, 3H. OCH$_3$), 4.02 (m, 1H, CH$_2$OH), 4.10 (m, 2H, CH$_2$OH); Mass Spectrum (APCI): m/e 800 (M+NH$_4$).

EXAMPLE 14

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6-formyl-7-(2-hydroxy-acetoxymethyl)-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene

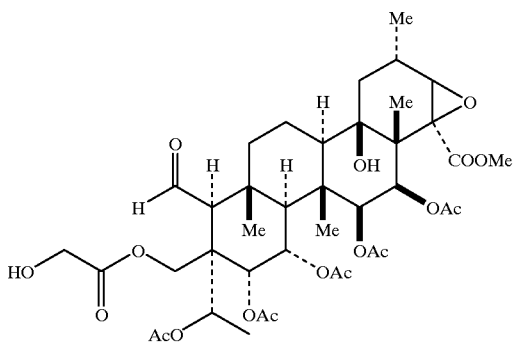

A solution of 200 mg of 4,6,7,15,16-pentakis(acetyloxy)-21,22-epoxy-18-hydroxy-22-methoxycarbonyl-D:A-Friedo-A-homo-27,30-dinor-24-oxaoleana-1-en-3-one in 20 mL of 1:1 CH$_2$Cl$_2$-methanol was cooled to 0° C. and a stream of ozone was passed through it. After 90 minutes the solution was purged with nitrogen for 15 min and divided in half. A spatual of 10% Pd/C was added to one portion and the solution was shaken under 25 psi of hydrogen for 18 h. The solution was filtered through Celite and concentrated to afford the title compound.

$^1$H NMR (CDCl$_3$) δ9.65 (d, 1H, J=4.5 Hz); Mass Spectrum (APCI): m/e 842 (M+NH$_4$).

EXAMPLE 15

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6-formyl-7-((2-acetoxyacetoxy) methyl)-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahvdrocryseno[1,2-b]oxirene

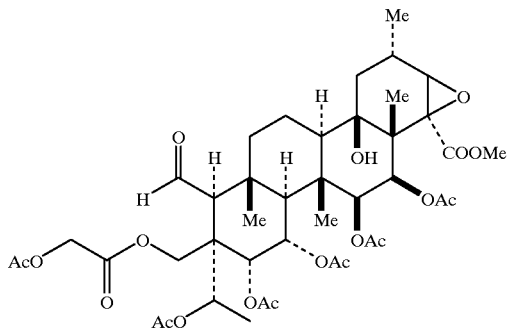

A solution of 200 mg of [1a-R-1aα, 2β, 3aβ, 3β, 5aβ, 6β, 7α, 7β, 8α, 9α9aα, 9bβ, 10β, 11β, 11aβ, 11bα, 11bβ]-7-(1-R-acetoxyethyl)-3 a-hydroxy-6-formyl-7-(2-hydroxy-acetoxymethyl)-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene, 76 uL of acetic anhydride, and 80 uL of pyridine in 5 mL of CH$_2$Cl$_2$ was stirred at room temperature. After 3 h, the solution was partitioned between ether and water and the organic layer was washed with water and brine, dried over MgSO$_4$, and concentrated. The residue was filtered through a pad of silica gel using 40% acetone-hexane to afford the title compound.

$^1$H NMR (CDCl$_3$) δ9.82 (d, 1H, J=4.5 Hz); Mass Spectrum (APCI): m/e 884 (M+NH$_4$).

EXAMPLE 16

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6-formyl-7-(2-hydroxy-acetoxymethyl)-11b-methoxycarbonyl-2-oxo-8, 9, 10, 11-tetraacetoxy-5a, 9b, 11a-trimethyl-1a, 2, 3, 3a, 3b, 4, 5, 5a, 6, 7, 8, 9, 9a, 9b, 10, 11, 11a, 11b-octadecahydrocryseno[1,2-b]oxirene

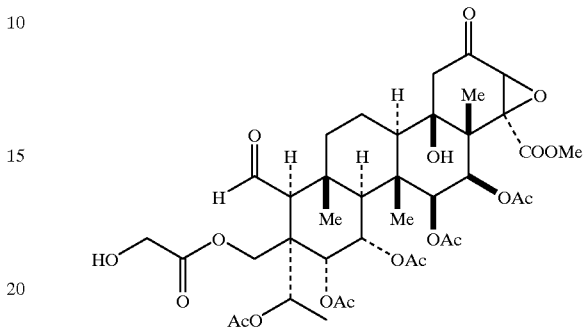

A solution of 300 mg of 4,6,7,15,16-pentakis(acetyloxy)-21,22-epoxy-18-hydroxy-22-methoxycarbonyl-D:A-Friedo-A-homo-27,30-dinor-24-oxaoleana-1, 20(29)-dien-3-one in 15 mL of 1:1 CH$_2$Cl$_2$-methanol was cooled to 0° C. and a stream of ozone was passed through it. After 90 minutes the solution was purged with nitrogen for 15 min and divided into three portions. A spatual of 10% Pd/C was added to one portion and the solution was shaken under 25 psi of hydrogen for 18 h. The solution was filtered through Celite and concentrated to afford the title compound.

$^1$H NMR (CDCl$_3$) δ9.76 (d, 1H, J=4.0Hz); Mass Spectrum (APCI): m/e 842 (M+NH$_4$).

EXAMPLE 17

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6, 7-bis-(acetoxymethyl)-11b-methoxycarbonyl-2, 8, 9, 10, 11-pentaacetoxy-5a, 9b, 11a-trimethyl-1a, 2, 3, 3a, 3b, 4, 5, 5a, 6, 7, 8, 9, 9a, 9b, 10, 11, 11a, 11b-octadecahydro-cryseno[1,2-b]oxirene

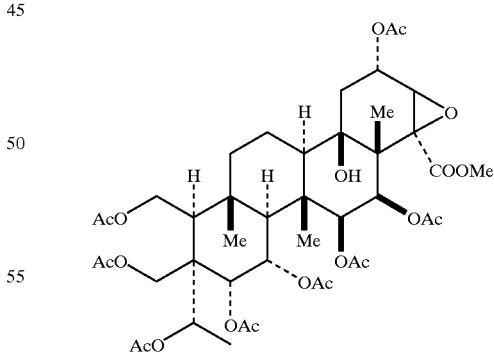

Part A: Preparation of [1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-2, 3a-dihydroxy-6, 7-bis-(hydroxymethyl)-11b-methoxycarbonyl-8, 9, 10, 11-tetraacetoxy-5a, 9b, 11a-trimethyl-1a, 2, 3, 3a, 3b, 4, 5, 5a, 6, 7, 8, 9, 9a, 9b, 10, 11, 11a, 11b-octadecahydro-cryseno[1,2-b]oxirene A solution of 1000 mg of 4,6,7,15,16-Pentakis (acetyloxy)-21,22-epoxy-18-hydroxy-22-methoxycarbonyl- D:A-Friedo-A-homo-27,30-dinor-24-oxaoleana-1, 20(29)-dien-3-one in 30 mL of CH₂Cl₂ and 30 mL of methanol was cooled to 0° C. and a stream of ozone was passed through it for 2 h. After the solution was purged with nitrogen for 10 min, it was allowed to warm to room temperature and 300 mg of NaBH₄ was added in small portions. After 1 h, the reaction was quenched with 50 mL of 1M HCl and the mixture was diluted with CH₂Cl₂. The layers were separated and the aqueous layer was washed with three portions of CH₂Cl₂. The organic extracts were combined, dried over MgSO₄, and concentrated.

The oily residue was dissolved in 5 mL of CH₂Cl₂ and the solution was cooled to 0° C. Then 1 mL of triethylsilane and 1 mL of BF3-etherate were added and the solution was stirred at 4° C. for 18 h. The reaction was quenched by adition of 20 mL of saturated NaHCO₃ solution and the mixture was diluted with CH₂Cl₂. The layers were separated and the aqueous layer was washed with CH₂Cl₂. The combined organic extracts were dried over MgSO₄ and concentrated. The residue was purified by flash chromatography (silica gel) using 2:1 ethyl acetate-hexane to afford the title compound.

Mass Spectrum (APCI): m/e788 (M+NH₄).

Part B: Preparation of [1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6, 7-bis-(acetoxymethyl)-11b-methoxycarbonyl-2, 8, 9, 10, 11-pentaacetoxy-5a, 9b, 11a-trimethyl-1a, 2, 3, 3a, 3b, 4, 5, 5a, 6, 7, 8, 9, 9a, 9b, 10, 11, 11a, 11b-octadecahydro-cryseno[1,2-b]oxirene A solution of 31 mg of [1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-2, 3a-dihydroxy-6, 7-bis-(hydroxymethyl)-11b-methoxycarbonyl-8, 9, 10, 11-tetraacetoxy-5a, 9b, 11a-trimethyl-1a, 2, 3, 3a, 3b, 4, 5, 5a, 6, 7, 8, 9, 9a, 9b, 10, 11, 11a, 11b-octadecahydrocryseno[1,2-b]oxirene in 0.5 mL pyridine and 0.25 mL of acetic anhydride was stirred at room temperature for 18 h. The solution was concentrated and the pyridine was removed by azeotropic distillation with three 5 mL portions of heptane. The oily residue was filtered through a silica gel Sep-Pak with 10 Ml of 4:1 ethyl acetate-hexane, then was purified by HPLC (Waters RCM, μ Porosil, 25 mm×10 cm) using a mixture of 8:4:1 hexane-methyl tert-butyl ether-acetonitrile to afford the title compound.

Mass Spectrum (APCI): m/e 914(M+NH₄).

EXAMPLE 18

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-7-(2-hydroxymethyl)-6-(3-hydroxypropylidene)-11b-methoxycarbonyl-2-oxo-8, 9, 10, 11-tetraacetoxy-5a, 9b, 11a-trimethyl-1a, 2, 3, 3a, 3b, 4, 5, 5a, 6, 7, 8, 9, 9a, 9b, 10, 11, 11a, 11b-octadecahydrocryseno[1,2-b]oxirene

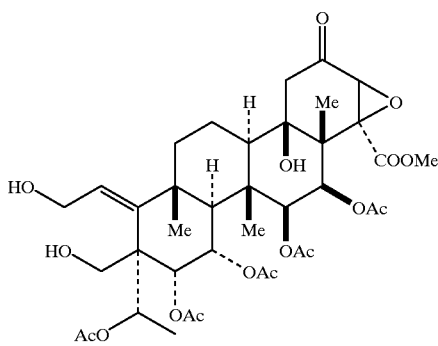

A solution of 200 mg of 4,6,7,15,16-pentakis(acetyloxy)-21,22-epoxy-18-hydroxy-22-methoxycarbonyl-D:A-Friedo-A-homo-27,30-dinor-24-oxaoleana-1, 3, 20(29)-triene in 20 mL of 1:1 CH₂Cl₂-methanol was cooled to 0° C. and a stream of ozone was passed through it. After 45 minutes the solution was purged with nitrogen for 15 min and a spatual of 10% Pd/C was added. The solution was shaken under 25 psi of hydrogen for 18 h, then the solution was filtered through Celite and concentrated. The residue was purified by HPLC (Waters RCM, 11 Porosil, 25 mm×10 cm) using a mixture of 8:4:1 hexane/methl t-butyl ether/acetonitrile to afford the title compound.

¹H NMR (CDCl₃) δ2.42, 2.79 (AB, 2H, J=15 Hz), 3.69, 3.98 (AB, 2H, J=12.5 Hz)), 4.15 (m, 1H), 4.62 (m, 1H); Mass Spectrum (APCI): m/e 798 (M+NH₄).

EXAMPLE 19

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-7-(2-acetoxyydroxymethyl)-6-(3-methoxy-3-oxopropylidene)-11b-methoxycarbonyl-2-oxo-8, 9, 10, 11-tetraacetoxy-5a, 9b, 11a-trimethyl-1a, 2, 3, 3a, 3b, 4, 5, 5a, 6, 7, 8, 9, 9a, 9b, 10, 11a, 11b-octadecahydrocryseno [1,2-b]oxirene

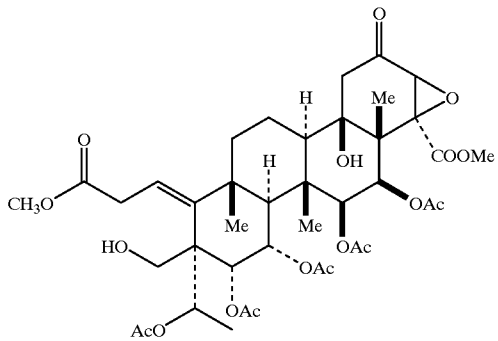

Further elution of the above column (Example 18), HPLC (Waters RCM, μ Porosil, 25 mm×10 cm), using a mixture of 8:4:1 hexane-methyl tert-butyl ether-acetonitrile afforded the title compound.

¹H NMR (CDCl₃) δ3.87 (m, 1H), 4.04 (m, 1H), 4.40 (m, 1H), 4.61 (m,1H), 5.73 (m, 1H); Mass Spectrum (APCI): m/e 840 (M+NH₄).

EXAMPLE 20

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-7-(formyloxymethyl)-6-(3-acetoxypropylidene)-11b-methoxycarbonyl-2-oxo-8, 9, 10, 11-tetraacetoxy-5a, 9b, 11a-trimethyl-1a, 2, 3, 3a, 3b, 4, 5, 5a, 6, 7, 8, 9, 9a, 9b, 10, 11, 11a, 11b-octadecahydrocryseno[1,2-b]oxirene

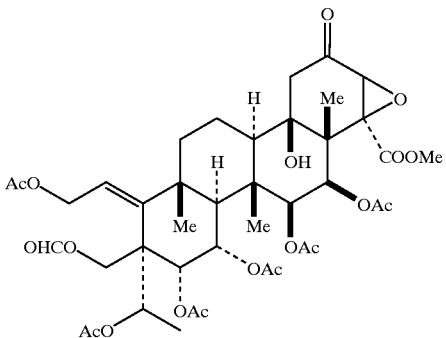

Part A: [1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-7-(formyloxymethyl)-6-(3-hydroxypropylidene)-11b-methoxycarbonyl-2-oxo-8, 9, 10, 11-tetraacetoxy-5a, 9b, 11a-trimethyl-1a, 2, 3, 3a, 3b, 4, 5, 5a, 6, 7, 8, 9, 9a, 9b, 10, 11, 11a, 11b-octadecahvdrocrvseno[1,2-b]oxirene Further elution of the above column (Example 19), HPLC (Waters RCM, µ Porosil, 25 mm×10 cm), using a mixture of 8:4:1 hexane-methyl tert-butyl ether-acetonitrile to afford the title compound.

$^1$H NMR (CDCl$_3$) δ7.96 (s, 1H); Mass Spectrum (APCI): m/e 826 (M+NH$_4$). Mass Spectrum (APCI): m/e 914(M+NH$_4$).

Part B: [1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-7-(formyloxymethyl)-6-(3-acetoxypropylidene)-11b-methoxycarbonyl-2-oxo-8, 9, 10, 11-tetraacetoxy-5a, 9b, 11a-trimethyl-1a, 2, 3, 3a, 3b, 4, 5, 5a, 6, 7, 8, 9, 9a, 9b, 10, 11, 11a, 11b-octadecahydrocryseno[1,2-b]oxirene A solution of 10.0 mg of [1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-7-(formyloxymethyl)-6-(3-hydroxypropylidene)-11b-methoxycarbonyl-2-oxo-8, 9, 10, 11-tetraacetoxy-5a, 9b, 11a-trimethyl-1a, 2, 3, 3a, 3b, 4, 5, 5a, 6, 7, 8, 9, 9a, 9b, 10, 11, 11a, 11b-octadecahydrocryseno[1,2-b]oxirene in 0.5 mL of pyridine and 0.25 mL of acetic anhydride was stirred at room temperature for 18 h. The solution was concentrated and the pyridine was removed by azeotropic distillation of heptane. The residue was purified by HPLC (Waters RCM, Porosil, 25 mm×10 cm), using a mixture of 8:4:1 hexane-methyl tert-butyl ether-acetonitrile to afford the title compound.

$^1$H NMR (CDCl$_3$) δ7.96 (s, 1H); Mass Spectrum (APCI): m/e 868 (M+NH$_4$).

EXAMPLE 21

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-7-(acetoxymethyl)-6-(3-methoxy-3-oxopropylidene)-11b-methoxycarbonyl-2-oxo-8, 9, 10, 11-tetraacetoxy-5a, 9b, 11a-trimethyl-1a, 2, 3, 3a, 3b, 4, 5, 5a, 6, 7, 8, 9, 9a, 9b, 10, 11, 11a, 11b-octadecahydrocryseno[1,2-b]oxirene

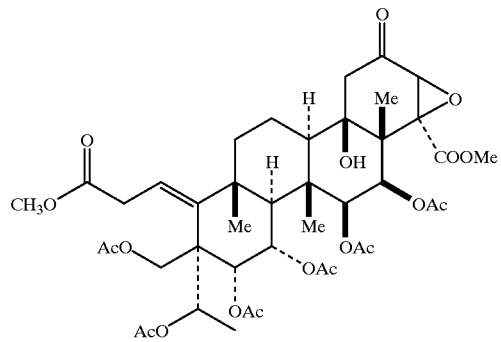

A solution of 4.0 mg of [1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-7-(2-hydroxymethyl)-6-(3-methoxy-3-oxopropylidene)-11b-methoxycarbonyl-2-oxo-8, 9, 10, 11-tetraacetoxy-5a, 9b, 11a-trimethyl-1a, 2, 3, 3a, 3b, 4, 5, 5a, 6, 7, 8, 9, 9a, 9b, 10, 11, 11a, 11b-octadecahydrocryseno[1,2-b]oxirene in 0.5 mL of pyridine and 0.25 mL of acetic anhydride was stirred at room temperature for 18 h. The solution was concentrated and the pyridine was removed by azeotropic distillation of heptane. The residue was purified by HPLC (Waters RCM, Porosil, 25 mm×10 cm), using a mixture of 8:4:1 hexane-methyl tert-butyl ether-acetonitrile to afford the title compound.

$^1$H NMR (CDCl$_3$) δ4.11 (m, 1H), 4.66 (m, 1H), 5.73 (m, 1H); Mass Spectrum (APCI): m/e 882 (M+NH$_4$).

EXAMPLE 22

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6, 7-bis-(methoxymethyl)-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydro-cryseno[1,2-b]oxirene

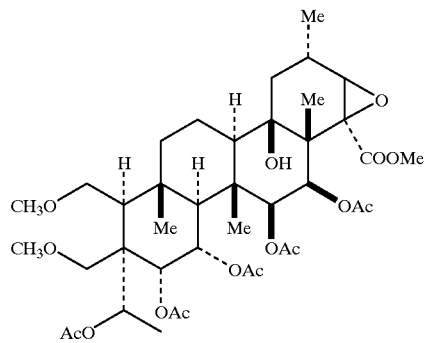

To a solution of 200 mg of [1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6, 7-bis-(hydroxymethyl)-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene in 1 mL of CH$_2$Cl$_2$ was added 1 mL of 2,6-di-t-butylpyridine and 0.5 mL of methyl triflate. The solution was stirred at 30° C. for 2h. The reaction was quenched by addition of 10 mL of saturated NaHCO$_3$ solution and 70 mL of CH$_2$Cl$_2$, then the layers were separated. The aqueous layer was washed twice with CH$_2$Cl$_2$ and the combined organic extracts were dried over MgSO$_4$ and concentrated. The residue was purified by HPLC (Waters RCM, μ Porosil, 25 mm×10 cm), using a mixture of 8:4:1 hexane-methyl tert-butyl ether-acetonitrile to afford the title compound.

$^1$H NMR (CDCl$_3$) δ3.33 (s, 3H), 3.36 (s, 3H); Mass Spectrum (APCI): m/e 814 (M+NH$_4$).

EXAMPLE 23

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6-methoxymethyl-7-hydroxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene

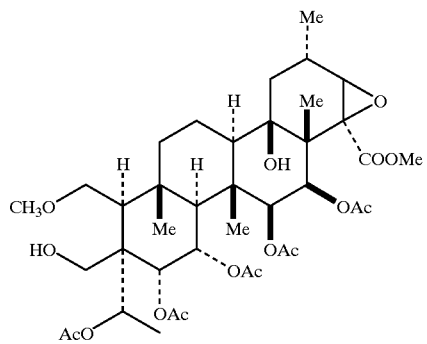

Further elution of the above column (Example 22) afforded the title compound. Mass Spectrum (APCI): m/e 800 (M+NH$_4$).

EXAMPLE 24

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6-hydroxymethyl-7-methoxymethyl-11b-methoxycarbonyl-8, 9, 10, 1 1-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene

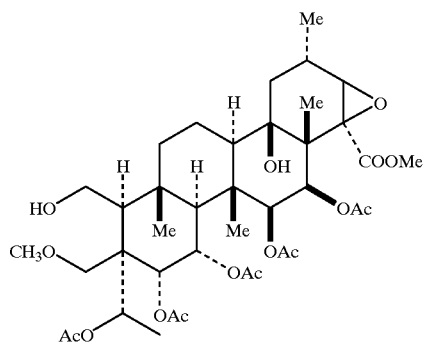

Further elution of the above column (Example 22) afforded the title compound. Mass Spectrum (APCI): m/e 800 (M+NH$_4$).

EXAMPLE 25

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6-methoxymethyl-7-ethoxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene

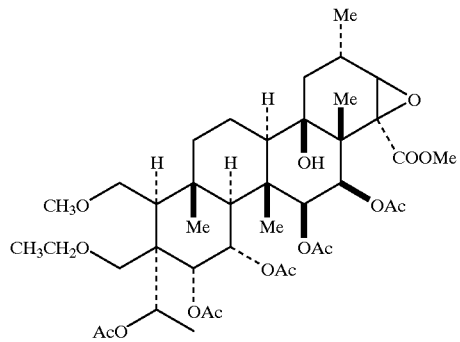

To a solution of 18 mg of [1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6-methoxymethyl-7-hydroxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene in 1 mL of CH$_2$Cl$_2$ was added 78 uL of 2,6-di-t-butylpyridine and 30 uL of methyl triflate. The solution was stirred at 40° C. for 18 h. The reaction was quenched by addition of 10 mL of saturated NaHCO$_3$ solution and 70 mL of CH$_2$Cl$_2$, then the layers were separated. The aqueous layer was washed twice with CH$_2$Cl$_2$ and the combined organic extracts were dried over MgSO$_4$ and concentrated. The residue was purified by HPLC (Waters RCM, μ Porosil, 25 mm×10 cm), using a mixture of 8:4:1 hexane-methyl tert-butyl ether-acetonitrile to afford the title compound. Mass Spectrum (APCI): m/e 828 (M+NH$_4$).

EXAMPLE 26

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6-methoxymethyl-7-benzyloxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene

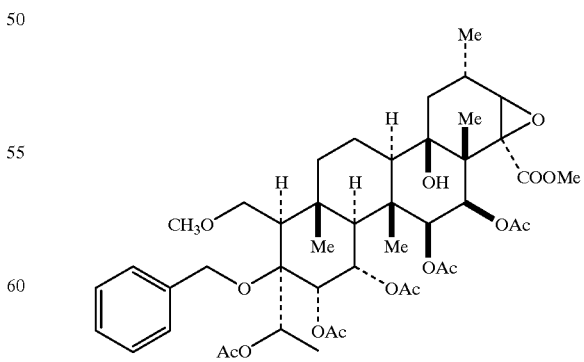

$^1$H NMR (CDCl$_3$) δ3.40 (s, 3H), 4.36, 4.60 (AB, 2H, J=17 Hz), 7.5–7.8 (m, 5H); Mass Spectrum (APCI): m/e 890 (M+NH$_4$).

EXAMPLE 27

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6-methoxymethyl-7-allyloxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene

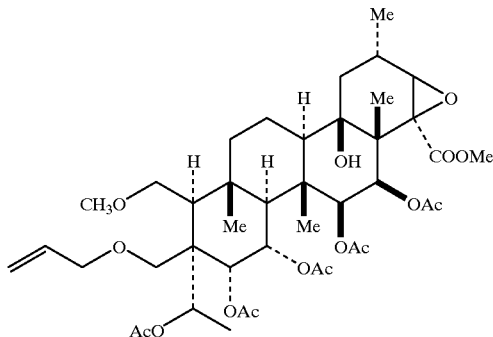

Mass Spectrum (APCI): m/e 840 (M+NH$_4$).

EXAMPLE 28

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6-methoxymethyl-7-acetoxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene

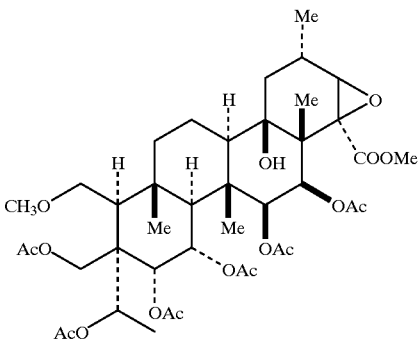

A solution of 16 mg of [1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-7-(2-acetoxyydroxymethyl)-6-(3-methoxy-3-oxopropylidene)-11b-methoxycarbonyl-2-oxo-8, 9, 10, 11-tetraacetoxy-5a, 9b, 11a-trimethyl-1a, 2, 3, 3a, 3b, 4, 5, 5a, 6, 7, 8, 9, 9a, 9b, 10, 11, 11a, 11b-octade-cahydrocryseno[1,2-b]oxirene in 0.5 mL of pyridine and 0.1 mL of acetic anhydride was stirred at room temperature for 18h. The solution was concentrated and the pyridine was removed by azeotropic distillation with heptane. The residue was purified by HPLC (Waters RCM, μ Porosil, 25 mm×10 cm), using a mixture of 8:4:1 hexane-methyl tert-butyl ether-acetonitrile to afford the title compound.

$^1$H NMR (CDCl$_3$) δ4.80, 4.23 (AB, 2H, J=12 Hz); Mass Spectrum (APCI): m/e 842 (M+NH$_4$).

EXAMPLE 29

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6-ethoxymethyl-7-methoxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene

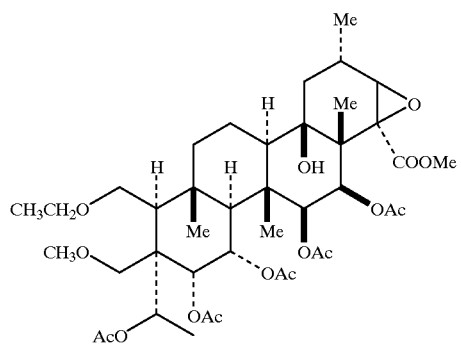

To a solution of 16 mg of [1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6-hydroxymethyl-7-methoxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene in 1 mL of CH$_2$Cl$_2$ was added 175 uL of 2,6-di-t-butylpyridine and 75 uL of methyl triflate. The solution was stirred at 40° C. for 18h. The reaction was quenched by addition of 10 mL of saturated NaHCO$_3$ solution and 70 mL of CH$_2$Cl$_2$, then the layers were separated. The aqueous layer was washed twice with CH$_2$Cl$_2$ and the combined organic extracts were dried over MgSO$_4$ and concentrated. The residue was purified by HPLC (Waters RCM, μ Porosil, 25 mm×10 cm), using a mixture of 8:4:1 hexane-methyl tert-butyl ether-acetonitrile to afford the title compound. Mass Spectrum (APCI): m/e 828 (M+NH$_4$).

EXAMPLE 30

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-(2-bromobenzyloxyethyl)-3a-hydroxy-6, 7-bis-(methoxymethyl)-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene

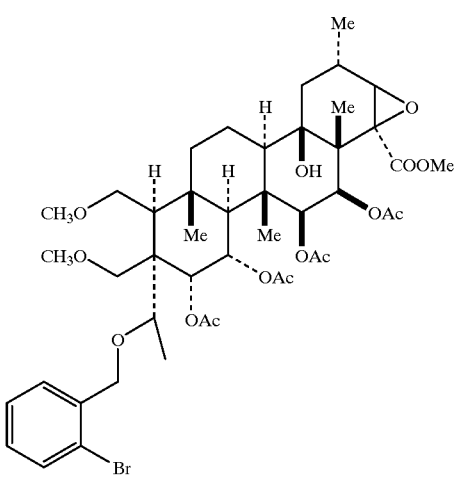

Part A: Preparation of [1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-(hydroxyethyl)-3a-hydroxy-6, 7-bis-(methoxymethyl)-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydro-cryseno[1,2-b]oxirene A solution of 50 mg of [1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-(acetoxyethyl)-3a-hydroxy-6, 7-bis-(methoxymethyl)-11b-methoxycarbonyl-8, 9, 10, 11-tetraacetoxy-2, 5a, 9b, 11a-tetramethyl-11a, 2, 3, 3a, 3b, 4, 5, 5a, 6, 7, 8, 9, 9a, 9b, 10, 11, 11a, 11b-octadecahydrocryseno[1,2-b]oxirene in 2 mL of tetrahydrofuran and 1 mL of 2M HCl was heated at 50° C. for 2 h. The solution was diluted with 20 mL of CH$_2$Cl$_2$, washed with saturated NaHCO$_3$, dried over MgSO$_4$, and concentrated. The residue was purified by HPLC (Waters RCM, μ Porosil, 25 mm×10 cm), using a mixture of 8:4:1 hexane-methyl tert-butyl ether-acetonitrile to afford the title compound.

$^1$H NMR (CDCl$_3$) δ4.52 (q, 2H, J=6.5 Hz); Mass Spectrum (APCI): m/e 772 (M+NH$_4$).

Part B: Preparation of [1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-(2-bromobenzyloxyethyl)-3a-hydroxy-6, 7-bis-(methoxymethyl)-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno [1,2-b]oxirene A solution of 153 mg of 2-bromobenzyl alcohol in 1 mL of dry CH$_2$Cl$_2$ was cooled to −78° C. under nitrogen. To this was added 86 uL of 2,6-di-t-butylpyridine and 37 μL of triflic anhydride. The solution was allowed to warm to 0° C. over 30 min, then was re-cooled to −78° C. A solution of 9.7 mg of [1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-hydroxyethyl)-3a-hydroxy-6, 7-bis-(methoxymethyl)-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene in 0.5 mL of CH$_2$Cl$_2$ was added and the solution was allowed to warm to 0° C. The reaction was quenched after 20 min by addition of 10 mL of saturated NaHCO$_3$ solution and 20 mL of ethyl acetat. The layers were separated, the aqueous layer was washed twice with CH$_2$Cl$_2$ and the combined organic extracts were dried over MgSO$_4$ and concentrated. The residue was purified by HPLC (Waters RCM, μ Porosil, 25 mm×10 cm), using a mixture of 8:4:1 hexane-methyl tert-butyl ether-acetonitrile to afford the title compound;

$^1$H NMR (CDCl$_3$) δ4.60, 4.71 (AB, 2H, J=12.5 Hz), 7.14 (t, 1H, J=7.5 Hz), 7.33 (t, 1H, 7.5 Hz), 7.53 (d, 1H, J=7.5 Hz), 7.62 (d, 1H, J=7.5 Hz); Mass Spectrum (APCI): m/e 939, 941 (M+NH$_4$).

EXAMPLE 31

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6, 7, 11b-tris-(methoxymethyl)-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene

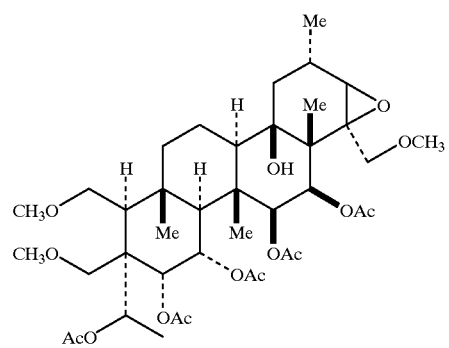

Part A: Preparation of [1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-(hydroxyethyl)-3a-hydroxy-6, 7,1 1b-tris-(hydroxymethyl)-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno-[1,2-b]oxirene A solution of 1.7 g of 4,6,7,15,16-pentakis(acetyloxy)-21, 22-epoxy-18-hydroxy-22-methoxycarbonyl-D:A-Friedo-A-homo-27,30-dinor-24-oxaoleana-1-en-3-one in 20 mL of CH$_2$Cl$_2$ and 20 mL of methanol was cooled to 0° C. and a stream of ozone was passed through it . After 3 h, the solution was purged with nitrogen for 15 min, then was allowed to warm to room temperature. A total of 1.1 g of NaBH$_4$ was added and the reaction mixture was left stirring for 18 h. Then and additional 1.1 g of NaBH$_4$ was added and the soution was stirred at room temperature for 2.5 h. The reaction was quenched with 50 mL of 1M HCl and the mixture was diluted with CH$_2$Cl$_2$. The layers were separated and the aqueous layer was washed with three portions of CH$_2$Cl$_2$. The organic extracts were combined, dried over MgSO$_4$, and concentrated. The oily residue was purified by flash chromatography (silica gel) using 2:1 ethyl acetate-petroleum ether to afford the title compound. Mass Spectrum (APCI): m/e 686 (M+NH$_4$).

Part B: Preparation of [1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-(2-aceoxyethyl)-3a-hydroxy-6, 7, 11-tris-(methoxymethyl)-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadeca-hydrocryseno[1,2-b]oxirene To a solution of 153 mg of [1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6, 7, 11b-tris-(hydroxymethyl)-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene in 1 mL of CH$_2$Cl$_2$ was added 1.3 mL of 2,6-di-t-butylpyridine and 0.4 mL of methyl triflate. The solution was stirred at 30° C. for 1 h. The reaction was quenched by addition of 10 mL of saturated NaHCO$_3$ solution and 70 mL of CH$_2$Cl$_2$, then the layers were separated. The aqueous layer was washed twice with CH$_2$Cl$_2$ and the combined organic extracts were dried over MgSO$_4$ and concentrated. The residue was purified by HPLC (Waters RCM, μ Porosil, 25 mm×10 cm), using a mixture of 8:4:1 hexane-methyl tert-butyl ether-acetonitrile to afford the title compound.

$^1$H NMR (CDCl$_3$) δ3.23 (s, 3H), 3.24 (s, 3H), 3.45 (s, 3H); Mass Spectrum (APCI): m/e 800 (M+NH$_4$).

EXAMPLE 32

[1a-R-1aα, 2β, 3aβ, 3β, 5aβ, 6β, 7α, 7β, 8α, 9α, 9aα, 9bβ, 10β, 11β, 11aβ, 11bα, 11bβ, ]-7-(1-R-acetoxyethyl)-3a-hydroxy-6-oxo-7-methoxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene

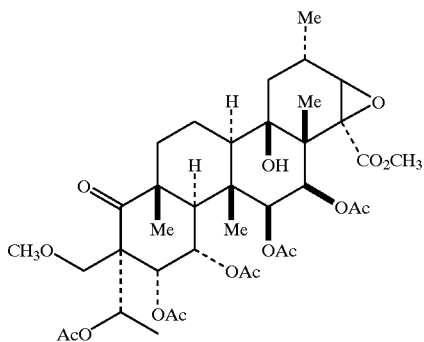

Part A: Preparation of 4,6,7,15,16-pentakis(acetyloxy)-21,22-epoxy-18-hydroxy-22-methoxycarbonyl-1-methylthio-[1α, 6α, 7α, 15β, 16β, 20β, 21β, 22β)-D:A-Friedo-2,3,27,30-tetranor-24-oxaoleanane

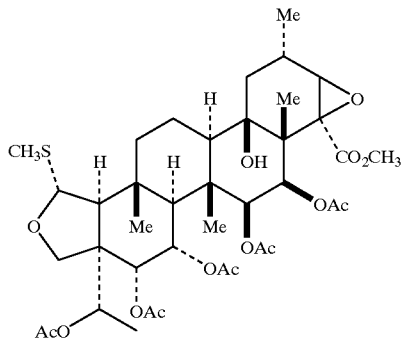

A solution of 900 mg of 4,6,7,15,16-pentakis(acetyloxy)-21,22-epoxy-1,18-dihydroxy-22-methoxycarbonyl-[1α, 6α, 7α, 15β, 16β, 20β, 21β, 22β)-D:A-Friedo-2,3,27,30-tetranor-24-oxaoleanane and 1.107 mL of trimethylsilylthiophenol in 20 mL of 0.5M ZnCl$_2$ in tetrahydrofuran was stirred at 45° C. for 18 h. The solution was partitioned between ether and water and the layers separated. The aqueous layer was washed with brine, and organic layer was dried over MgSO$_4$ and concentrated. The residue was purified by flash chromatography (silica gel) using 2:1 ethyl acetate-hexane to afford the title compound.

$^1$H NMR (CDCl$_3$) δ2.35 (s, 3H, —SCH$_3$); Mass Spectrum (APCI): m/e 876 (M+NH$_4$).

Part B: Preparation of 4,6,7,15,16-pentakis(acetyloxy)-21,22-epoxy-18-hydroxy-22-methoxycarbonyl-1-methylsulfinyl-[1α, 6α, 7α, 15β, 16β, 20β, 21β, 22β)-D:A-Friedo-2,3,27,30-tetranor-24-oxaoleanane

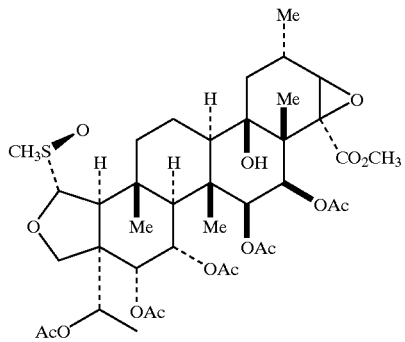

A solution of 960 mg of 4,6,7,15,16-pentakis(acetyloxy)-21,22-epoxy-18-hydroxy-22-methoxycarbonyl-1-methylthio-[1α, 6α, 7α, 15β, 16β, 20β, 21β, 22β)-D:A-Friedo-2,3,27,30-tetranor-24-oxaoleanane in 20 mL of dry CH$_2$Cl$_2$ was cooled to 0° C. To this was added 393 mg of 3-chloroperbenzoic acid and the solution was stirred at 0° C. for 90 min. The solution was washed with two portions of saturated NaHCO$_3$, dried over MgSO4, and concentrated. The residue was purified by flash chromatography (silica gel) using 1:1 ethyl acetate-hexane to afford the title compound.

$^1$H NMR (CDCl$_3$) δ2.31 (s, 3H, —SCH$_3$); Mass Spectrum (APCI): m/e 892(M+NH$_4$).

Part C: Preparation of 4,6,7,15,16-pentakis(acetyloxy)-21,22-epoxy-18-hydroxy-22-methoxycarbonyl-[1α, 6α, 7α, 15β, 16β, 20β, 21β, 22β)-D:A-Friedo-2,3,27,30-tetranor-24-oxaoleana-1-ene

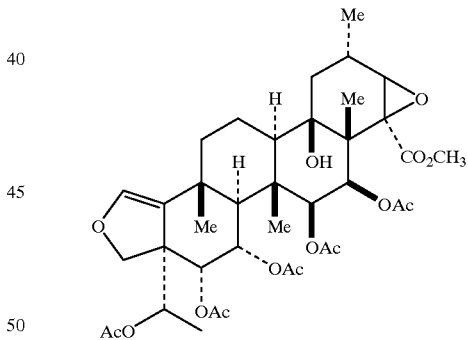

A solution of 550 mg of 4,6,7,15,16-pentakis(acetyloxy)-21,22-epoxy-18-hydroxy-22-methoxycarbonyl-1-methysulfinyl-[1α, 6α, 7α, 15β, 16β, 20β, 21β, 22β)-D:A-Friedo-2,3,27,30-tetranor-24-oxaoleanane in 20 mL of dry xylenes was heated under reflux (bath temperature 150° C.) for 18 h. The solution was concentrated and the residue was purified by flash chromatography (silica gel) using 1:1 ethyl acetate-hexane to afford the title compound.

$^{13}$C NMR (CDCl$_3$) δ129.4, 142.0; Mass Spectrum (APCI): m/e 766 (M+NH$_4$).

Part D: Preparation of 4,6,7,15,16-pentakis(acetyloxy)-21,22-epoxy-1, 10, 18-trihydroxy-22-methoxycarbonyl-[1α, 6α, 7α, 15β, 16β, 20β, 21β, 22β)-D :A-Friedo-2,3,27,30-tetranor-24-oxaoleanane

63

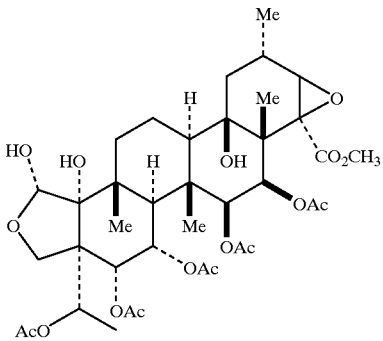

A solution of 300 mg of 4,6,7,15,16-pentakis(acetyloxy)-21,22-epoxy-18-hydroxy-22-methoxycarbonyl-[1α, 6α, 7α, 15β, 16β, 20β, 21β, 22β)-D:A-Friedo-2,3,27,30-tetranor-24-oxaoleana-1-ene in 10 mL of CH$_2$Cl$_2$ was cooled to 0° C. Then a stream of ozone was bubbled into the solution for 10 minutes. The reaction was quenched by addition of 1 mL of methyl sulfide and the solution was concentrated. The residue was purified by flash chromatography (silica gel) using 2:1 ethyl acetate-hexane to afford the title compound.

$^{13}$C NMR (CDCl$_3$) δ98.0; Mass Spectrum (APCI): m/e 800 (M+NH$_4$).

Part E: [1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-7-formyloxymethyl-6-oxo-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene

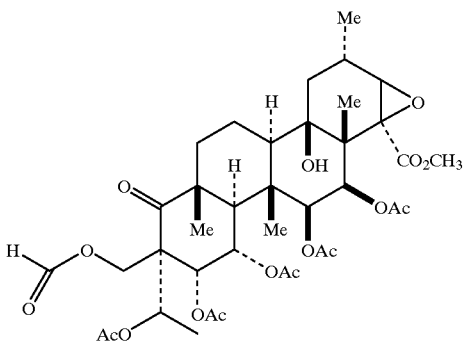

A solution of 10 mg of 4,6,7,15,16-pentakis(acetyloxy)-21,22-epoxy-1, 10, 18-trihydroxy-22-methoxycarbonyl-[1α, 6α, 7α, 15β, 16β, 20β, 21β, 22β)-D:A-Friedo-2,3,27,30-tetranor-24-oxaoleanane and 10 mg of periodic acid in 0.25 mL of tetrahydrofuran was stirred at room temperature. After 4 h, the solution was diluted with ether, washed with water, saturated NaHCO3 solution, 1M HCl, and brine, and dried over MgSO4. The solution was concentrated to afford the title compounds.

$^1$H NMR (CDCl$_3$) δ7.96 (s, 1H); 13C NMR (CDCl$_3$) δ160, 210.5; Mass Spectrum (APCI): m/e 798 (M+NH$_4$).

Part F: [1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-7-hydroxymethyl-6-oxo-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene

64

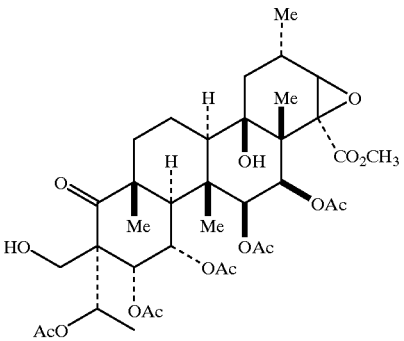

A solution of 50 mg of [1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-7-formyloxymethyl-6-oxo-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene and 100 mg silica gel in 3 mL of methanol was stirred at room temperature. After 18 h, the solution was filtered and concentrated to afford the title compound. $^{13}$C NMR (CDCl$_3$) δ212; Mass Spectrum (APCI): m/e 770 (M+NH$_4$).

Part G: [1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-7-methoxymethyl-6-oxo-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno-[1,2-b]oxirene

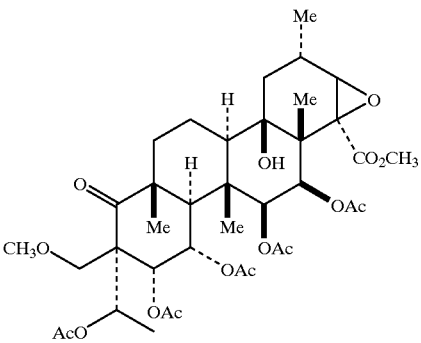

A solution of 45 mg of [1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-7-hydroxymethyl-6-oxo-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene , 396 uL of 2,6-di-t-butylpyridine, and 100 uL of methyl triflate in 3 mL of CH$_2$Cl$_2$ was stirred at 45° C. After 18 h the reaction was quenched by addition of 10 mL of saturated NaHCO$_3$ solution and 70 mL of CH$_2$Cl$_2$, then the layers were separated. The aqueous layer was washed twice with CH$_2$Cl$_2$ and the combined organic extracts were dried over MgSO$_4$ and concentrated. The residue was purified by HPLC (Waters RCM, μ Porosil, 25 mm×10 cm), using a mixture of 8:4:1 hexane-methyl tert-butyl ether-acetonitrile afford the title compound.

$^1$H NMR (CDCl$_3$) δ3.02, 3.77 (AB, 2H, JAB=8 Hz), 3.22 (s, 3H); $^{13}$ C NMR (CDCl$_3$) δ212; Mass Spectrum (APCI): m/e 784 (M+NH$_4$)

EXAMPLE 33

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-6-methoxymethyl-7-formy-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene

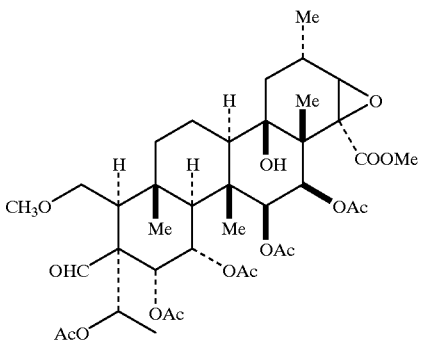

A solution of 150 ,L of oxalyl chloride in 1 mL of $CH_2Cl_2$ was cooled to $-78°$ C. under nitrogen. To this was added a solution of 225 uL of dimethyl sulfoxide in 2 mL of $CH_2Cl_2$ and the solution was stirred at $-78°$ C. After 15 minutes a solution of 50 mg of [1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-6-methoxymethyl-7-hydroxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene in 1 mL of $CH_2Cl_2$ was added and the solution was stirred at $-78°$ C. for 45 minutes. Then 890 uL of triethylamine was added and the solution was stirred for 90 min. The reaction mixture was partitioned between $CH_2Cl_2$ and water and the organic layer was washed with 1M HCl, saturated $NaHCO_3$ solution and brine, dried over $MgSO_4$, and concnetrated. The residue was filtered through silica gel using 2:1 ethyl acetate-hexane to afford the title compound.

$^1$H NMR ($CDCl_3$) δ9.85 (s, 1H); Mass Spectrum (APCI): m/e 812 (M +$NH_4$).

What is claimed is:

1. A compound of structural Formula I:

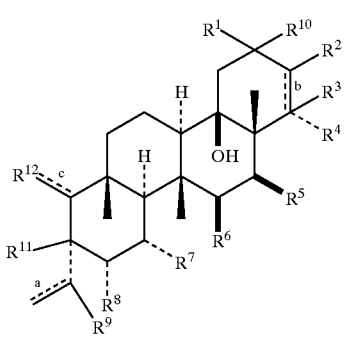

or a pharmaceutically acceptable salt, crystal form, or hydrate, wherein:

a, b and c are independently a single bond or a double bond, and represented by ≡≡≡ in the structure above:

n is: 0, 1 or 2;
r is: 0 or 1;
s is: 0 or 1;
$R^1$ and $R^{10}$ are independently:
  (1) hydroxyl,
  (2) ($C_1$–$C_6$)-alkyloxy,
  (3) H,
  (4) OCO($C_1$–$C_6$)-alkyl,
  (5) ($C_1$–$C_6$)-alkyl,
  (6) $R^1$ and $R^{10}$ taken together is an exo-methylene group,
  (7) $R^1$ and $R^{10}$ taken together is =O, or
  (8) $R^1$ and $R^{10}$ taken together is an oxirane group;
$R^2$ and $R^3$ are independently:
  (1) hydroxyl,
  (2) ($C_1$–$C_6$)-alkyloxy,
  (3) H,
  (4) OCO($C_1$–$C_6$)-alkyl,
  (5) ($C_1$–$C_6$)-alkyl,
  (6) phenyl, or
  (7) $R^2$ and $R^3$ taken together is an oxirane group when b is a single bond,
or $R^2$ is =O when b is a single bond;
$R^4$ is:
  (1) $CO_2$($C_1$–$C_6$)-alkyl,
  (2) $CO_2H$,
  (3) $CH2OH$,
  (4) C(=O) $NR^{13}R^{14}$,
  (5) ($C_1$–$C_6$)-alkyl,
  (6) $CH_2O$($C_1$–$C_6$)-alkyl, or
  (7) CHO;
$R^5$, $R^6$, $R^7$ and $R^8$ are independently selected from the group consisting of:
  (1) $O[(C=O)O_r]_sR^{13}$,
  (2) $O[(C=O)O_r]_s$-aryl, aryl as defined below, and
  (3) $O[(C=O)O_r]_s$-heteroaryl, heteroaryl as defined below;
$R^9$ is:
  (1) H,
  (2) OH,
  (3) =O when a is a single bond,
  (4) $O[(C=O)O_r]_s$($C_1$–$C_6$)-alkyl, alkyl as defined below,
  (5) $O[(C=O)O_r]_s$($C_2$–$C_6$)-alkenyl, as defined below,
  (6) $O[(C=O)O_r]_s$-aryl, aryl as defined below,
  (7) $O[(C=O)O_r]_s$-heteroaryl, heteroaryl as defined below,
  (8) $O(CH_2)_n$-heteroaryl, heteroaryl as defined below, or
  (9) $O(CH_2)_n$-aryl, aryl as defined below,
$R^{11}$ is chosen from the group consisting of:
  (1) H,
  (2) $O(CH_2)_n$-heteroaryl, wherein heteroaryl is defined as an unsubstituted, monosubstituted, or disubstituted five or six membered aromatic heterocycle containing from 1 to 3 heteroatoms selected from the group consisting of O, N and S and wherein the substituents are selected from the group consisting of:
    (a) halo, wherein halo is fluoro, chloro, bromo, or iodo,
    (b) hydroxy,
    (c) ($C_1$–$C_6$)-alkyl,
    (d) ($C_1$–$C_4$)-perfluoroalkyl,
    (e) ($C_1$–$C_6$)-alkenyl,
    (f) ($C_1$–$C_6$)-alkynyl,
    (g) ($C_1$–$C_6$)-alkyloxy, (h) $(C_1-C_6)$-alkyl-S(O)$_n$-,
(i) phenyl,
(j) phenoxy,
(k) cyano,
(l) nitro,
(m) $CO_2H$,
(n) $CO(C_1-C_6)$-alkyl,
(o) $CO_2(C_1-C_6)$-alkyl,
(p) $CONR^{13}R^{14}$,
(q) $NR^{13}R^{14}$,
(r) $NR^{13}CO(C_1-C_6)$-alkyl,
(s) fused benzo, and
(t) fused pyridyl group,
(3) $O(CH_2)_n$-aryl, wherein aryl is defined as phenyl or naphthyl, unsubstituted or substituted with one, two or three of the substituents selected from the group consisting of:
(a) halo, wherein halo is fluoro, chloro, bromo, or iodo,
(b) hydroxy,
(c) $(C_1-C_6)$-alkyl,
(d) $(C_1-C_4)$-perfluoroalkyl,
(e) $(C_1-C_6)$-alkenyl,
(f) $(C_1-C_6)$-alkynyl,
(g) $(C_1-C_6)$-alkyloxy,
(h) $(C_1-C_6)$-alkyl-S(O)$_n$-,
(i) phenyl,
(j) phenoxy,
(k) cyano,
(l) nitro,
(m) $CO_2H$,
(n) $CO(C_1-C_6)$-alkyl,
(o) $CO_2(C_1-C_6)$-alkyl,
(p) $CONR^{13}R^{14}$,
(q) $NR^{13}R^{14}$,
(r) $NR^{13}CO(C_1-C_6)$-alkyl,
(s) $(C_1-C_6)$-alkenyloxy, and
(t) benzyloxy;
(4) $(C_1-C_6)$-alkyl, wherein alkyl is unsubstituted or substituted with one or two of the substituents selected from the group consisting of:
(a) halo, wherein halo is fluoro, chloro, bromo, or iodo,
(b) hydroxy,
(c) oxo,
(d) $(C_1-C_6)$-alkyloxy,
(e) $(C_1-C_6)$-S(O)$_n$-,
(f) aryl-$(C_1-C_6)$-alkyloxy,
(g) cyano,
(h) nitro,
(i) vinyl,
(j) $NR^{13}R^{14}$,
(k) $NR^{13}CO(C_1-C_6)$-alkyl,
(l) CHO,
(m) $CO_2H$,
(n) $CO(C_1-C_6)$-alkyl,
(o) $CO_2(C_1-C_6)$-alkyl,
(p) $CONR^{13}R^{14}$,
(q) aryl, as defined above, and
(r) $OCOCH_3$,
(5) $(CH_2)_nO(C_1-C_6)$-alkyl, wherein alkyl is as defined above,
(6) $(C_2-C_6)$-alkenyl, wherein alkenyl is unsubstituted or substituted with one or two of the substituents selected from the group consisting of:
(a) halo, wherein halo is fluoro, chloro, bromo, or iodo,
(b) hydroxy,
(c) oxo,
(d) $(C_1-C_6)$-alkyloxy,
(e) $(C_1-C_6)$-S(O)$_n$-,
(f) phenyl-$(C_1-C_6)$-alkyloxy,
(g) cyano,
(h) nitro,
(i) vinyl,
(j) $NR^{13}R^{14}$,
(k) $NR^{13}CO(C_1-C_6)$-alkyl,
(l) CHO,
(m) $CO_2H$,
(n) $CO(C_1-C_6)$-alkyl,
(o) $CO_2(C_1-C_6)$-alkyl,
(p) $CONR^{13}R^{14}$,
(q) aryl, wherein aryl is as defined above,
(r) heteroaryl, wherein heteroaryl is as defined above, and
(s) $OCOCHC_3$,
(7) $(CH_2)_nO(C_2-C_6)$-alkenyl, wherein alkenyl is as defined above,
(8) CHO,
(9) COOH,
(10) $CONR^{13}R^{14}$,
(11) $O[(C=O)O_r]_s(C_1-C_6)$-alkyl, alkyl as defined above,
(12) $(CH_2)_nS(C_1-C_6)$-alkyl, wherein alkyl is as defined above,
(13) $(CH_2)_nS(C_2-C_6)$-alkenyl, wherein alkenyl is as defined above, or
(14) $(CH_2)_nS(C_2-C_6)$-aryl, wherein aryl is as defined above;
$R^{12}$ is as defined above for $R^{11}$ when c is a single bond, or
$R^{12}$ is as defined below when c is a double bond:
(1) =O,
(2) =CH-$(C_1-C_6)$-alkyl, wherein alkyl is as defined above,
(3) =CH-$(C_1-C_6)$-alkenyl, wherein alkenyl is as defined above, or
(4) =CH-aryl, wherein aryl is as defined above;
$R^{13}$ and $R^{14}$ are independently:
(1) hydrogen,
(2) $(C_1-C_6)$-alkyl, or
(3) phenyl.
2. The compound of structural Formula I as recited in claim 1, wherein
b is a single bond;
$R^1$ and $R^{10}$ are independently:
(1) hydroxyl,
(2) $(C_1-C_6)$-alkyl,
(3) $R^1$ and $R^{10}$ taken together is an exo-methylene group,
(4) $R^1$ and $R^{10}$ taken together is =O, or
(5) $R^1$ and $R^{10}$ taken together is an oxirane group;
$R^2$ and $R^3$ are taken together to be an oxirane group;
R4 is:
(1) $CO_2(C_1-C_6)$-alkyl, wherein alkyl is defined above, or
(2) $CH_2O(C_1-C_6)$-alkyl;
$R^5$, $R^6$, $R^7$ and $R^8$ are $OCO(C_1-C_6)$-alkyl;
$R^9$ is:
(1) $O[(C=O)O_r]_s(C_1-C_6)$-alkyl, alkyl as defined below,
(2) $O[(C=O)O_r]_s(C_2-C_6)$-alkenyl, as defined below,
(3) $O[(C=O)O_r]_s$-aryl, aryl as defined below,

69

(4) O[(C=O)O$_r$]s-heteroaryl, heteroaryl as defined below,
(5) O(CH$_2$)$_n$-heteroaryl, heteroaryl as defined below, or
(6) O(CH$_2$)$_n$-aryl, aryl as defined below, R$^{11}$ and R$^{12}$ are independently chosen from the group consisting of:
(1) H,
(2) O(CH$_2$)$_n$-aryl, wherein aryl is defined as phenyl or naphthyl, unsubstituted or substituted with one, two or three of the substituents selected from the group consisting of:
 (a) halo, wherein halo is fluoro, chloro, bromo, or iodo,
 (b) hydroxy,
 (c) (C$_1$–C$_6$)-alkyl,
 (d) (C$_1$–C$_4$)-perfluoroalkyl,
 (e) (C$_1$–C$_6$)-alkyloxy,
 (f) cyano, and
 (g) nitro,
(3) (C$_1$–C$_6$)-alkyl, wherein alkyl is unsubstituted or substituted with one or two of the substituents selected from the group consisting of:
 (a) halo, wherein halo is fluoro, chloro, bromo, or iodo,
 (b) hydroxy,
 (c) oxo,
 (d) (C$_1$–C$_6$)-alkyloxy,
 (e) CHO,
 (f) CO$_2$H,
 (g) CO$_2$(C$_1$–C$_6$)-alkyl,
 (h) CONR$^{13}$R$^{14}$,
 (i) aryl, as defined above, and
 (j) OCOCH$_3$,
(4) (CH$_2$)$_n$O(C$_1$–C$_6$)-alkyl, wherein alkyl is as defined above,
(5) (C$_2$–C$_6$)-alkenyl, wherein alkenyl is unsubstituted or substituted with one or two of the substituents selected from the group consisting of:
 (a) halo, wherein halo is fluoro, chloro, bromo, or iodo,
 (b) hydroxy,
 (c) oxo,
 (d) (C$_1$–C$_6$)-alkyloxy,
 (e) CHO,
 (f) CO$_2$H,
 (g) CO$_2$(C$_1$–C$_6$)-alkyl,
 (h) CONR$^{13}$R$^{14}$,
 (i) aryl, as defined above, and
 (j) OCOCH$_3$,
(6) (CH$_2$)$_n$(C$_2$–C$_6$)-alkenyl, wherein alkenyl is as defined above,
(7) CHO,
(8) COOH,
(9) CONR$^{13}$R$^{14}$,
(10) O[(C=O)O$_r$]$_s$(C$_1$–C$_6$)-alkyl, alkyl as defined above,
(11) (CH$_2$)$_n$S(C$_1$–C$_6$)-alkyl, wherein alkyl is as defined above,
(12) (CH$_2$)$_n$S(C$_2$–C$_6$)-alkenyl, wherein alkenyl is as defined above, or
(13) (CH$_2$)$_n$S(C$_2$–C$_6$)-aryl, wherein aryl is as defined above;

op R is any of the following when c is a double bond:
(1) =O,
(2) =CH—(C$_1$–C$_6$)-alkyl, wherein alkyl is as defined above,
(3) =CH—(C$_1$–C$_6$)-alkenyl, wherein alkenyl is as defined above, or

70

(4) =CH—(C$_1$–C$_6$)-aryl, wherein aryl is as defined above;

R$^{13}$ and R$^{14}$ are independently:
(1) hydrogen,
(2) (C$_1$–C$_6$)-alkyl, or
(3) phenyl.

3. The compound of structural Formula I as recited in claim 2, wherein
R$^1$ and R$^{10}$ are independently:
 (1) (C$_1$–C$_3$)-alkyl,
 (2) R$^1$ and R$^{10}$ taken together is an exo-methylene group,
 (3) R$^1$ and R$^{10}$ taken together is =O, or
 (4) R$^1$ and R$^{10}$ taken together is an oxirane group;
R$^2$ and R$^3$ are taken together to be an oxirane group;
R$^4$ is:
 (1) CO$_2$(C$_1$–C$_3$)-alkyl, wherein alkyl is methyl, ethyl, or propyl, or
 (2) CH$_2$O(C$_1$–C3)-alkyl, wherein alkyl is methyl, ethyl, or propyl;
R$^5$, R$^6$, R$^7$ and R$^8$ are O(C=O)CH$_3$;
R$^9$ is:
 (1) O(C=O)(C$_1$–C$_3$)-alkyl, wherein alkyl is methyl, ethyl, or propyl, or
 (6) O(CH$_2$)-aryl, wherein aryl is phenyl or naphthyl unsubstituted or substituted with one or two substitutents selected from the following: F, Cl, Br, I, methyl, ethyl, propyl, and hydroxyl;
R$^{11}$ and R$^{12}$ are independently chosen from the group consisting of:
 (1) O(CH$_2$)-phenyl, wherein phenyl is unsubstituted or substituted with one or two of the substituents selected from the group consisting of:
  (a) halo, wherein halo is fluoro, chloro, bromo, or iodo,
  (b) hydroxy,
  (c) (C$_1$–C$_6$)-alkyl,
  (d) (C$_1$–C$_4$)-perfluoroalkyl,
  (e) (C$_1$–C$_6$)-alkyloxy,
  (f) cyano, and
  (g) nitro,
 (2) (C$_1$–C$_3$)-alkyl, wherein alkyl is unsubstituted or substituted with one or two of the substituents selected from the group consisting of:
  (a) halo, wherein halo is fluoro, chloro, bromo, or iodo,
  (b) hydroxy,
  (c) oxo,
  (d) (C$_1$–C$_3$)-alkyloxy,
  (e) CHO,
  (f) CO$_2$H,
  (g) CO$_2$(C$_1$–C$_3$)-alkyl, wherein alkyl is methyl, ethyl, or propyl,
  (h) CONR$^{13}$R$^{14}$,
  (i) phenyl, as defined above, and
  (j) OCOCH$_3$,
 (3) (CH2)O(C$_1$–C$_3$)-alkyl, wherein alkyl is methyl, ethyl, or propyl,
 (4) (C$_2$–C$_3$)-alkenyl, wherein alkenyl is unsubstituted or substituted with one or two of the substituents selected from the group consisting of:
  (a) halo, wherein halo is fluoro, chloro, bromo, or iodo,
  (b) hydroxy,
  (c) oxo,
  (d) (C$_1$–C$_6$)-alkyloxy, (e) CHO,
(f) CO$_2$H,
(g) CO$_2$(C$_1$–C$_6$)-alkyl,
(h) CONR$^{13}$R$^{14}$,
(i) aryl, as defined above, and
(j) OCOCH$_3$,
(5) (CH$_2$)O(C$_2$–C$_3$)-alkenyl, wherein alkenyl is defined as vinyl or allyl,
(6) CHO,
(7) COOH,
(8) CONR$^{13}$R$^{14}$, and
(9) O(C=O)H;
or R$^{12}$ is any of the following when c is a double bond:
(1) =O, or
(2) =CH—(C$_1$–C$_3$)-alkyl, wherein alkyl is as defined above,
R$^{13}$ and R$^{14}$ are independently:
(1) hydrogen,
(2) (C$_1$–C$_3$)-alkyl, wherein alkyl is defined as methyl, ethyl, or propyl, or
(3) phenyl.

4. A compound selected from the group consisting of:

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-6, 7-bis-(hydroxymethyl)-11b-methoxycarbonyl-8, 9, 10, 11-tetraacetoxy-2, 5a, 9b, 11a-tetramethyl-1a, 2, 3, 3a, 3b, 4, 5, 6a, 6, 7, 8, 9, 9a, 9b, 10, 11, 1a, 11b-octadecahydrocryseno[1,2-b] oxirene,

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-2-epoxymethylidene-3a-hydroxy-6, 7-bis-(hydroxymethyl)-11b-methoxycarbonyl-8, 9, 10, 11-tetraacetoxy-5a, 9b, 11a-trimethyl-1a, 3, 3a, 3b, 4, 5, 5a, 6, 7, 8, 9, 9a, 9b, 10, 11, 11a, 11b-hexadecahydrocryseno [1,2-b]oxirene,

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-6-formyl-7-((2-acetoxyacetoxy) methyl)-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-6-formyl-7-(2-hydroxy-acetoxymethyl)-11b-methoxycarbonyl-2-oxo-8, 9, 10, 11-tetraacetoxy-5a, 9b, 11a-trimethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-6, 7-bis-(acetoxymethyl)-11b-methoxycarbonyl-2, 8, 9, 10, 11-pentaacetoxy-5a, 9b, 11a-trimethyl-1a, 2, 3, 3a, 3b, 4, 5, 5a, 6, 7, 8, 9, 9a, 9b, 10, 11, 11a, 11b-octadecahydrocryseno [1,2-b]oxirene,

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-7-(2-acetoxyydroxymethyl)-6-(3-methoxy-3-oxopropylidene)-11b-methoxycarbonyl-2-oxo-8, 9, 10, 11-tetraacetoxy-5a, 9b, 11a-trimethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-6, 7-bis-(methoxymethyl)-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno [1,2-b]oxirene,

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-6-methoxymethyl-7-hydroxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-6-hydroxymethyl-7-methoxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno [1,2-b]oxirene,

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-6-methoxymethyl-7-ethoxymethyl-11b-methoxycarbonyl-8, 9, 10, 11-tetraacetoxy-2, 5a, 9b, 11 a-tetramethyl-1a, 2, 3, 3a, 3b, 4, 5, 5a, 6, 7, 8, 9, 9a, 9b, 10, 11, 11a, 11b-octadecahydrocryseno [1,2-b]oxirene,

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-6-methoxymethyl-7-benzyloxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-6-methoxymethyl-7-allyloxymethyl-11b-methoxycarbonyl-8, 9, 10, 11-tetraacetoxy-2, 5a, 9b, IIa-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-6-methoxymethyl-7-acetoxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno [1,2-b]oxirene,

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-6-ethoxymethyl-7-methoxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-(2-bromobenzyloxyethyl)-3a-hydroxy-6, 7-bis-(methoxymethyl)-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno[1,2-b]oxirene,

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-6, 7, 11b-tris-(methoxymethyl)-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno [1,2-b]oxirene, and

[1a-R-1aα, 2β, 3aβ, 3β, 5aβ, 6β, 7α, 7β, 8α, 9α, 9aα, 9bβ, 10β, 11β, 11aβ, 11bα, 11bβ]-7-(1-R-acetoxyethyl)-3a-hydroxy-6-oxo-7-methoxymethyl-11b-methoxycarbonyl-8, 9, 10, 11-tetraacetoxy-2, 5a, 9b, 11a-tetramethyl-1a, 2, 3, 3a, 3b, 4, 5, 5a, 6, 7, 8, 9, 9a, 9b, 10, 11, 11a, 11b-octadecahydrocryseno [1,2-b] oxirene.

5. A compound of structural Formula II.

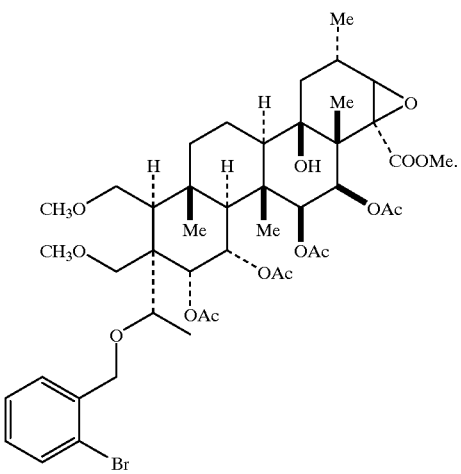

6. A compound of structural Formula III.

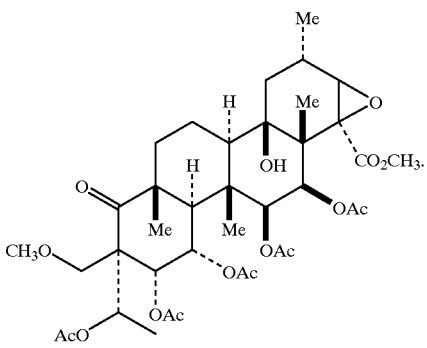

7. A method of treating a condition in a mammal in need thereof, the treatment of which is effected or facilitated by $K_v1.3$ inhibition, comprising the administration, in an amount that is effective at inhibiting $K_v1.3$, of a compound of Formula I, as recited in claim 1 to said mammal.

8. A method of claim 7 wherein the mammal is in need of preventing or treating the resistance to transplantation or transplantation rejection of organs or tissues.

9. A method of claim 7 wherein the mammal is in need of suppressing the immune system.

10. A pharmaceutical formulation comprising a pharmaceutically acceptable carrier and a therapeutically effective amount of the compound of Formula I, as recited in claim 1 or a pharmaceutically acceptable crystal form or hydrate thereof.

11. The pharmaceutical formulation of claim 10, comprising in addition, a second immunosuppressive agent selected from a group consisting of azathioprine, brequinar sodium, deoxyspergualin, mizaribine, mycophenolic acid morpholino ester, cyclosporin, FK-506 and rapamycin.

12. The method of claim 8, further comprising the coadministration of an effective amount of a second immunosuppressive agent to the mammal in need thereof.

13. A method of treating a condition in a mammal in need thereof, the treatment of which is effected or facilitated by $K_v1.3$ inhibition, comprising the administration to said mammal a pharmaceutical formulation comprising a pharmaceutical carrier and a compound of Formula I, as recited in claim 1, in an amount that is effective at inhibiting $K_v1.3$.

14. A method of treating a condition in a mammal in need thereof, the treatment of which is effected or facilitated by $K_v1.3$ inhibition, comprising the coadministration to said mammal of a therapeutically effective amount of a compound of formula I, as recited in claim 1, with an effective amount of a second immunosuppressive agent.

15. The method of claim 12 wherein the second immunosuppressive agent is chosen from the group consisting of azathioprine, brequinar sodium, deoxyspergualin, mizaribine, mycophenolic acid morpholino ester, cyclosporin, FK-506 and rapamycin.

* * * * *